United States Patent
Schoenafinger et al.

(10) Patent No.: US 7,612,104 B2
(45) Date of Patent: Nov. 3, 2009

(54) BICYCLIC ARYL-SULFONIC ACID [1,3,4]-THIADIAZOL-2-YL-AMIDES, PROCESSES FOR THEIR PREPARATION, PHARMACEUTICAL COMPOSITIONS AND METHODS FOR THEIR USE

(75) Inventors: Karl Schoenafinger, Alzenau (DE); Stefanie Keil, Frankfurt am Main (DE); Matthias Urmann, Frankfurt am Main (DE); Hans Matter, Frankfurt am Main (DE); Maike Glien, Frankfurt am Main (DE); Wolfgang Wendler, Frankfurt am Main (DE)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/062,759

(22) Filed: Apr. 4, 2008

(65) Prior Publication Data
US 2008/0293780 A1     Nov. 27, 2008

Related U.S. Application Data

(63) Continuation of application No. PCT/EP2006/009300, filed on Sep. 26, 2006.

(30) Foreign Application Priority Data
Oct. 6, 2005    (EP)    ................... 05021785

(51) Int. Cl.
A61K 31/433    (2006.01)
C07D 285/135   (2006.01)

(52) U.S. Cl. ....................... 514/363; 548/138
(58) Field of Classification Search .......... None
See application file for complete search history.

(56) References Cited

U.S. PATENT DOCUMENTS 3,565,897 A * 2/1971 Heerdt et al. ............... 544/297
5,097,669 A   3/1992 Hargrove et al.

FOREIGN PATENT DOCUMENTS

EP    1277729    1/2003

WO    WO 2005/005421    1/2005

OTHER PUBLICATIONS

"Metabolic Syndrome." American Heart Association. <http://www.americanheart.org/presenter.jhtml?identifier=4756> Accessed Mar. 30, 2009.*
Grundy et al. "Diagnosis and Management of the Metabolic Syndrome: An American Heart Association/National Heart, Lung, and Blood Institute Scientific Statement." Circulation 112 (2005), pp. 2735-2752.*
Mathur, Ruchi. "Metabolic Syndrome." MedicineNet.com. <http://www.medicinenet.com/metabolic_syndrome/article.htm> Accessed Mar. 31, 2009.*
Rubenstrunk et al. "Safety issues and prospects for future generations of PPAR modulators." Biochimica et Biophysica Acts 1771 (2007) 1065-1081.*

* cited by examiner

Primary Examiner—Rei-Tsang Shiao
Assistant Examiner—Alicia L Fierro
(74) Attorney, Agent, or Firm—Jiang Lin

(57) ABSTRACT

The present invention comprises bicyclic aryl-sulfonic acid [1,3,4]-thiadiazol-2-yl-amides, their functional derivatives thereof as well as their physiologically acceptable salts and pharmaceutical compositions thereof that exhibit peroxisome proliferator activated receptor (PPAR) PPARdelta and PPAR-gamma agonist activity. The structure of the compounds of the invention are defined by Formula I below,

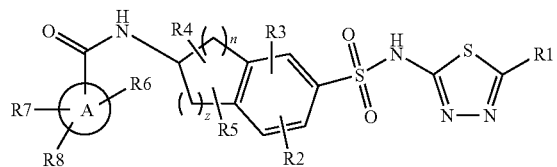

Formula I wherein the various substituents are defined herein, including their physiologically acceptable salts. Processes for the compounds preparation are also disclosed. The compounds are suitable for the treatment of fatty acid metabolism and glucose utilization disorders, disorders relating to insulin resistance are involved as well as demyelinating and other neurodegenerative disorders of the central and peripheral nervous system.

17 Claims, No Drawings

BICYCLIC ARYL-SULFONIC ACID [1,3,4]-THIADIAZOL-2-YL-AMIDES, PROCESSES FOR THEIR PREPARATION, PHARMACEUTICAL COMPOSITIONS AND METHODS FOR THEIR USE

CROSS-REFERENCE TO RELATED APPLICATIONS

This application is a continuation of International Patent Application No. PCT/EP2006/009300 filed on Sep. 26, 2006 which is incorporated herein by reference in its entirety which also claims the benefit of priority of European Patent Application No. 05021785.0 filed on Oct. 6, 2005.

FIELD OF THE INVENTION

The present invention relates generally to pharmaceutical compositions for the treatment of metabolic disorders and the diseases and physiological problems resulting there from. More specifically, the present invention relates to compounds which are able to therapeutically modulate lipid and/or carbohydrate metabolism in mammals and are thus suitable for the prevention and/or treatment of diseases such as type-2 diabetes, atherosclerosis, cardiovascular disorders and the like. The inventive compounds of the present invention are also useful in the treatment of the demyelinating and other neurodegenerative disorders of the central and peripheral nervous systems.

BACKGROUND OF THE INVENTION

Peroxisome proliferator activated receptor (PPAR) agonists are well known and have been described in the prior art, (see U.S. Pat. No. 6,200,995 to De La Brouse-Elwood et. al.; WO 03/043997 to Johnston et. al. and WO 01/00603 and WO 02/092590 to Keil et. al.) Benzenesulfonamino compounds which bind to PPARs are described in WO 2005/005421. Sulfonamide compounds comprising showing hypoglycemic activity are disclosed in Khimiko-Farmatsevticheskii Zhurnal (1987), 21(8), 965-8. From WO 97/40017 compounds having a phenyl group linked to heterocycles are known as modulators of molecules with phosphotyrosine recognition units.

The present invention comprises pharmaceutical compounds and compositions that therapeutically modulate lipid and/or carbohydrate metabolism and are thus suitable for the prevention and/or treatment of diseases such as type-2 diabetes, atherosclerosis and the physiological manifestations thereof. These compounds are also therapeutically effective in the treatment of demyelinating and other neurodegenerative disorders of the central and peripheral nervous systems. More specifically, the compounds of the present invention modulate the activity of peroxisome proliferator activated receptors (PPAR). The compounds are suitable in particular for activating PPARdelta or PPARdelta and PPARgamma receptors, however, the relative activation of each respective compound varies depending on the specific compound administered.

Peroxisome proliferator-activated receptors (PPAR) are transcription factors which can be activated by ligands and belong to the class of nuclear hormone receptors. There are three PPAR isoforms, PPARalpha, PPARgamma and PPARdelta (identical to PPARbeta), which are encoded by different genes (Peroxisome proliferator-activated receptor (PPAR): structure, mechanisms of activation and diverse functions: Motojima K., Cell Struct Funct., 1993, 18(5), 267-77).

In humans, PPARgamma exists in three variants, PPAR-gamma$_1$, gamma$_2$, and gamma$_3$, which are the result of alternative use of promoters and differential mRNA splicing. Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, the PPARalpha receptor plays an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effects and pathophysiology, see: Berger, J. et al., Annu. Rev. Med., 2002, 53, 409-435; Wilson, T. et al., J. Med. Chem., 2000, 43 (4), 527-550; Kliewer, S. et al., Recent Prog Horm Res., 2001, 56, 239-63; Moller, D. E. and Berger, J. P., Int J Obes Relat Metab Disord., 2003, 27 Suppl 3, 17-21; Ram, V. J., Drugs Today, 2003, 39(8), 609-32).

Among the three PPAR-isoforms the physiological functions of PPARdelta have long remained an enigma. The first proposed pharmacological role for PPARdelta has been the regulation of cholesterol homeostasis. It was shown that the somewhat selective PPARdelta ligand L-165041 raises plasma cholesterol in a diabetic animal model (Berger J. et al., J. Biol. Chem., 1999, 274, 6718-6725; Leibowitz M. D. et al., FEBS Lett., 2000, 473(3), 333-336). In obese, insulin resistant rhesus monkeys, the potent and selective PPARdelta ligand GW501516 raises HDL-cholesterol, decreases plasma LDL-cholesterol, triglycerides and insulin levels (Oliver, W. et al., Proc. Natl. Acad. Sci., 2001, 98, 5306-5311). The dual PPARdelta/PPARalpha agonist YM-16638 significantly lowers plasma lipids in rhesus and cynomolgus monkeys (Goto, S. et al., Br. J. Pharm., 1996, 118, 174-178) and acts in a similar manner in two weeks clinical trials in healthy volunteers (Shimokawa, T. et al., Drug Dev. Res., 1996, 38, 86-92). More recent publications underline that PPARdelta is an important target for the treatment of dyslipidemia, insulin resistance, type 2 diabetes, atherosclerosis and syndrome X (Wang, Y-X. et al., Cell, 2003, 113, 159-170; Luquet, S. et al., FASEB J., 2003, 17, 209-226; Tanaka, T. et al., PNAS, 2003, 100, 15924-15929; Hoist, D. et al., BioChem. Biophys. Acta, 2003, 1633, 43-50; Dressel, U. et al., Mol. Endocrin., 2003, 17, 2477-2493; Lee, C. H. et al., Science, 2003, 302, 453-457).

Besides its actions as a regulator of the lipid-, glucose- and cholesterol-metabolism PPARdelta is known to play a role in embryonic development, implantation and bone formation (Lim, H. and Dey, S. K., Trends Endocrinol Metab., 2000, 11(4), 137-42; Ding, N. Z. et al., Mol Reprod Dev., 2003, 66(3), 218-24; Mano, H. et al., J Biol Chem., 2000, 275(11), 8126-32).

Numerous publications demonstrate that PPARdelta is triggering proliferation and differentiation of keratinocytes which points to its role in skin disorders and wound healing (Di-Poi, N. et al., J Steroid Biochem Mol Biol., 2003, 85(2-5), 257-65; Tan, N. S. et al., Am J Clin Dermatol., 2003, 4(8), 523-30; Wahli, W., Swiss Med Wkly., 2002, 132(7-8), 83-91).

PPARdelta appears to be significantly expressed in the CNS; however much of its function there still remains undiscovered. Of singular interest however, is the discovery that PPARdelta was expressed in rodent oligodendrocytes, the major lipid producing cells of the CNS (J. Granneman, et al., J. Neurosci. Res., 1998, 51, 563-573). Moreover, it was also found that a PPARdelta selective agonist was found to significantly increase oligodendroglial myelin gene expression and myelin sheath diameter in mouse cultures (I. Saluja et al., Glia, 2001, 33, 194-204). Thus, PPARdelta activators may be of use for the treatment of demyelinating and dysmyelinating diseases. The use of peroxisome proliferator activated receptor delta agonists for the treatment of MS and other demyelinating diseases can be shown as described in WO2005/097098.

Demyelinating conditions are manifested in loss of myelin—the multiple dense layers of lipids and protein which cover many nerve fibers. These layers are provided by oligodendroglia in the central nervous system (CNS), and Schwann cells in the peripheral nervous system (PNS). In patients with demyelinating conditions, demyelination may be irreversible; it is usually accompanied or followed by axonal degeneration, and often by cellular degeneration. Demyelination can occur as a result of neuronal damage or damage to the myelin itself—whether due to aberrant immune responses, local injury, ischemia, metabolic disorders, toxic agents, or viral infections (Prineas and McDonald, Demyelinating Diseases. In Greenfield's Neuropathology, 6.sup.th ed. (Edward Arnold: New York, 1997) 813-811, Beers and Berkow, eds., The Merck Manual of Diagnosis and Therapy, 17.sup.th ed. (Whitehouse Station, N.J.: Merck Research Laboratories, 1999) 1299, 1437, 1473-76, 1483).

Central demyelination (demyelination of the CNS) occurs in several conditions, often of uncertain etiology, that have come to be known as the primary demyelinating diseases. Of these, multiple sclerosis (MS) is the most prevalent. Other primary demyelinating diseases include adrenoleukodystrophy (ALD), adrenomyeloneuropathy, AIDS-vacuolar myelopathy, HTLV-associated myelopathy, Leber's hereditary optic atrophy, progressive multifocal leukoencephalopathy (PML), subacute sclerosing panencephalitis, Guillian-Barre syndrome and tropical spastic paraparesis. In addition, there are acute conditions in which demyelination can occur in the CNS, e.g., acute disseminated encephalomyelitis (ADEM) and acute viral encephalitis. Furthermore, acute transverse myelitis, a syndrome in which an acute spinal cord transection of unknown cause affects both gray and white matter in one or more adjacent thoracic segments, can also result in demyelination. Also, disorders in which myelin forming glial cells are damaged including spinal cord injuries, neuropathies and nerve injury. The invention relates to bicyclic arylsulfonic acid [1,3,4]thiadiazol-2-yl-amides, functional derivatives thereof and their physiologically acceptable salts and physiologically showing PPAR agonistic activity.

SUMMARY OF THE INVENTION

The compounds of the present invention modulate the activity of peroxisome proliferator activated receptors (PPAR). The compounds are suitable in particular for activating PPARdelta or PPARdelta and PPARgamma receptors, and thereby are able to modulate lipid and/or carbohydrate metabolism and are thus suitable for the prevention and/or treatment of diseases such as type-2 diabetes, atherosclerosis and the physiological manifestations thereof. These compounds are also therapeutically effective in the treatment of demyelinating and other neurodegenerative disorders of the central and peripheral nervous systems. Specifically, the compounds of the present invention consist of N-[1,3,4]-thiadiazol-2-yl-benzene sulfonamides, and pharmaceutical compositions thereof as defined by the structure of formula I:

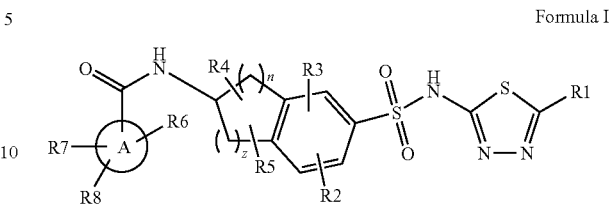

Formula I wherein the various substituent groups are defined herein.

DETAILED DESCRIPTION OF THE INVENTION

Compounds of the present invention are described by formula I:

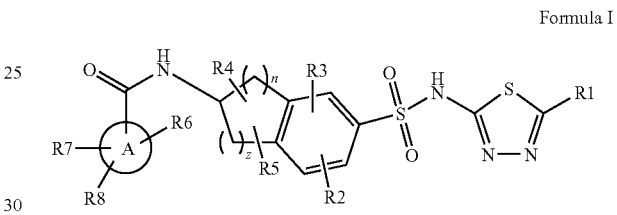

Formula I wherein

R1 is selected from the group consisting of (C1-C6)alkyl, (C0-C6)alkylene-(C3-C6)cycloalkyl, (C0-C6)alkylene-O—(C1-C6)alkyl, (C0-C6)alkylene-O—(C3-C6)cycloalkyl, (C0-C6)alkylene-(C6-C14)aryl and (C0-C6) alkylene-(C5-C15)heteroaryl, wherein alkyl, alkylene, aryl, heteroaryl and cycloalkyl can be unsubstituted or mono, di- or tri substituted by F, Cl, Br, $OCF_3$, CN, CO—(C1-C6)alkyl, COO(C1-C6)alkyl, CON((C0-C6)alkylene-H)((C0-C6)alkylene-H), $S(O)_m$(C1-C6)alkyl;

R2, R3, R4 and R5 are independently selected from the group consisting of H, halogen, (C1-C6)alkyl, (C0-C4)alkylene-O—(C0-C4)alkylene-H, CN, COO(C1-C6)alkyl, CON((C0-C6)alkylene-H)((C0-C6)alkylene-H), $S(O)_m$(C1-C6)alkyl, wherein alkyl and alkylene are unsubstituted or mono, di- or trisubstituted by F;

A is (C6-C14)aryl or (C4-C10) heteroaryl;

n is 1, 2 or 3;

m, z are 0, 1 or 2;

R6, R7 and R8 are independently selected from the group consisting of H, (C1-C6)alkyl, CN, CO—(C1-C6)alkyl, COO—(C1-C6)alkyl, CON((C0-C6)alkylene-H((C0-C6) alkylene-H), $S(O)_m$(C1-C6)alkyl, N((C0-C6)alkylene-H) ((C0-C6)alkylene-H), N((C0-C6)alkylene-H)—CO—(C1-C6)alkyl, N((C0-C6)alkylene-H)—CO—(C1-C6) alkyl, halogen, (C0-C6)alkylene-O—(C0-C6)alkylene-H, (C0-C6)alkylene-(C6-C14)aryl, (C0-C6)alkylene-O—(C6-C14)aryl, SCF3, S(O)2CF3 and NO2, wherein alkyl, aryl and alkylene are unsubstituted or mono, di- or trisubstituted by F and aryl can be unsubstituted or monosubstituted by CF3;

its' stereoisomers, enantiomers, tautomers, physiologically acceptable salts and mixtures thereof.

Another embodiment according to the invention are compounds of the formula 1, where
R1 is selected from the group consisting of (C1-C6)alkyl, (C0-C6)alkylene-(C3-C6)cycloalkyl, (C0-C6)alkylene-O—(C1-C6)alkyl, (C0-C6)alkylene-O—(C3-C6)cycloalkyl, (C0-C6)alkylene-(C6-C14)aryl, wherein alkyl, alkylene, aryl, and cycloalkyl can be unsubstituted or mono, di- or tri substituted by F, Cl, Br;
R2, R3, R4 and R5 are independently selected from the group consisting of H, halogen, (C1-C6)alkyl, (C0-C4)alkylene-O—(C0-C4)alkylene-H, wherein alkyl and alkylene are unsubstituted or mono, di- or trisubstituted by F;
A is selected from the group consisting of (C6-C14)aryl or (C4-C10) heteroaryl;
n is 1, 2;
z is 1, 2;
R6, R7 and R8 are independently selected from the group consisting of H, (C1-C6)alkyl, CN, halogen, (C0-C6)alkylene-O—(C0-C6)alkylene-H, (C0-C6)alkylene-(C6-C14)aryl, (C0-C6)alkylene-O—(C6-C14)aryl, SCF3 and S(O)2CF3, wherein alkyl, aryl and alkylene are unsubstituted or mono, di- or trisubstituted by F and aryl can be unsubstituted or monosubstituted by CF3;

its' stereoisomers, enantiomers, tautomers, physiologically acceptable salts and mixtures thereof.

A second embodiment of the present invention are compounds of formula 1, wherein
R1 is selected from the group consisting of (C1-C6)alkyl, (C0-C6)alkylene-(C3-C6)cycloalkyl, (C0-C6)alkylene-(C6-C14)aryl, wherein alkyl, alkylene, aryl, and cycloalkyl can be unsubstituted or mono, di- or tri substituted by F;
R2, R3, R4 and R5 are independently selected from the group consisting of H, halogen, (C1-C6)alkyl, and (C0-C4)alkylene-O—(C0-C4)alkylene-H, wherein alkyl and alkylene are unsubstituted or mono, di- or trisubstituted by F;
A is selected from the group consisting of (C6-C14)aryl or (C4-C10) heteroaryl;
n is 1, 2;
z is 1;
R6, R7 and R8 are independently selected from the group consisting of H, (C1-C6)alkyl, CN, halogen, (C0-C6)alkylene-O—(C6-C14)aryl, (C0-C6)alkylene-O—(C0-C6)alkylene-H, wherein alkyl and alkylene are unsubstituted or mono, di- or trisubstituted by F and aryl can be unsubstituted or monosubstituted by CF3;

its' stereoisomers, enantiomers, tautomers, physiologically acceptable salts and mixtures thereof.

Another embodiment of the present invention are compounds of the formula 1, wherein
R1 is selected from the group consisting of (C1-C6)alkyl, (C0-C6)alkylene-(C3-C6)cycloalkyl and (C0-C6)alkylene-(C6-C14)aryl, wherein alkyl, alkylene, aryl, and cycloalkyl can be unsubstituted or mono, di- or tri substituted by F;
R2, R3, R4 and R5 are independently selected from the group consisting of H, halogen, (C1-C6)alkyl, (C0-C4)alkylene-O—(C0-C4)alkylene-H, wherein alkyl and alkylene are unsubstituted or mono, di- or trisubstituted by F;
A is selected from the group consisting of phenyl, pyridine or thiophene;
n is 1;
z is 1;
R6 is F, Cl, Br, or O(C1-C4)-alkyl in the ortho position and;
R7 F, Cl, Br, CH3 or CF3 in the para position and;
R8 is H;

its' stereoisomers, enantiomers, tautomers, physiologically acceptable salts and mixtures thereof.

Yet another embodiment of the present invention are compounds of formula 1, wherein
R1 is selected from the group consisting of (C1-C4)alkyl, (C0-C2)alkylene (C3-C6)cycloalkyl and (C0-C2)alkylene-(C6-C10)aryl, wherein alkyl, aryl, and cycloalkyl can be unsubstituted or mono, di- or trisubstituted by F;
R2 is selected from the group consisting of H, halogen, (C1-C6)alkyl and O—(C0-C4)alkylene-H, wherein alkyl and alkylene are unsubstituted or mono, di- or trisubstituted by F;
R3 is H;
R4 is H;
R5 is H, (C1-C4)alkyl;
A is (C6)aryl or (C5-C6) heteroaryl;
n is 1, 2;
z is 1;
R6 is selected from the group consisting of (C1-C4)alkyl, halogen, (C0-C2)alkylene-O—(C0-C6)alkylene-H, (C0-C2)alkylene-(C6-C10)aryl, wherein alkyl, aryl and alkylene are unsubstituted or mono, di- or trisubstituted by F and aryl can be unsubstituted or monosubstituted by CF3;
R7 is selected from the group consisting of H, (C1-C4)alkyl, halogen, wherein alkyl is unsubstituted or mono, di- or trisubstituted by F;
R8 is H, F;

its' stereoisomers, enantiomers, tautomers, physiologically acceptable salts and mixtures thereof.

Another embodiment of the present invention are compounds of formula 1, where
R1 is selected from the group consisting of (C1-C4)alkyl, (C3-C6)cycloalkyl, phenyl, wherein alkyl can be unsubstituted or mono, di- or tri substituted by F;
R2 is selected from the group consisting of H, F, Cl, O—(C1-C4)alkylene-H, wherein alkylene is unsubstituted or mono, di- or trisubstituted by F;
R3 is H;
R4 is H;
R5 is H, (C1-C4)alkyl;
A is phenyl, thiophene, thiazole, pyridine;
n is 1, 2;
z is 1;
R6 is selected from the group consisting of (C1-C4)alkyl, F, Cl, O—(C0-C6)alkylene-H, phenyl, wherein phenyl can be unsubstituted or monosubstituted by CF3;
R7 is selected from the group consisting of H, (C1-C4)alkyl, Cl, wherein alkyl is unsubstituted or mono, di- or trisubstituted by F;
R8 is H or F;

its' stereoisomers, enantiomers, tautomers, physiologically acceptable salts and mixtures thereof.

Another embodiment according to the invention are compounds of formula 1, wherein
R1 is selected from the group consisting of ethyl, isopropyl, tert. butyl, cyclopropyl, cyclohexyl, phenyl and trifluoromethyl;
R2, R3, R4 and R5 are selected from the group consisting of H, F, Cl, OCH3 and OCH2CF3;
A is phenyl;
n is 1;
z is 1;
R6 is selected from the group consisting of Cl, Br, or O(C1-C2)-alkyl and is in the ortho position
R7 is Cl, Br or CF3 and is in the para position and;
R8 is H;

its' stereoisomers, enantiomers, tautomers, physiologically acceptable salts and mixtures thereof.

Another embodiment according to the invention are compounds of formula 1, where
R1 is isopropyl;
R2, R3, R4 and R5 are H;
A is phenyl;
n is 1;
z is 1;
R6 is O(C1-C2)-alkyl and in ortho position;
R7 is Cl or CF3 and in the para position and;
R8 is H;

its' stereoisomers, enantiomers, tautomers, physiologically acceptable salts and mixtures thereof.

Another embodiment according to the invention are compounds of formula 1, where
R1 is trifluoromethyl;
R2, R3, R4 and R5 are H;
A is phenyl;
n is 1;
z is 1;
R6 is O-ethyl and in ortho position;
R7 is Cl or CF3 and in the para position and;
R8 is H;

its' stereoisomers, enantiomers, tautomers, physiologically acceptable salts and mixtures thereof.

Another embodiment of the present invention are compounds of formula 1, where
R1 is cyclohexyl;
R2, R3, R4 and R5 are H;
A is phenyl;
n is 1;
z is 1;
R6 is O-ethyl and in the ortho position;
R7 is Cl or CF3 and in the para position,
R8 is H its' stereoisomers, enantiomers, tautomers, physiologically acceptable salts and mixtures thereof.

Another embodiment of the present invention are compounds of formula 1, where
R1 is phenyl;
R2, R3, R4 and R5 are H;
A is phenyl;
n is 1;
z is 1;
R6 is O-ethyl and in ortho position;
R7 is Cl or CF3 and in the para position and;
R8 is H;

its' stereoisomers, enantiomers, tautomers, physiologically acceptable salts and mixtures thereof.

Still another embodiment according to the present invention are compounds of formula 1, where
R1 is cyclopropyl;
R2, R3, R4 and R5 are H;
A is phenyl;
n is 1;
z is 1;
R6 is O-ethyl and in ortho position;
R7 is in para position and Cl or CF3;
R8 is H;

its' stereoisomers, enantiomers, tautomers, physiologically acceptable salts and mixtures thereof.

Another embodiment according to the invention are compounds of the formula 1, where
R1 is isopropyl;
R2, R3, R4 and R5 are H;
A is thiophene;
n is 1;
z is 1;
R6 is O-ethyl and in ortho position;
R7 is Cl or CF3 and in para position;
R8 is H;

its' stereoisomers, enantiomers, tautomers, physiologically acceptable salts and mixtures thereof.

Preferably, the present invention comprises the compounds:
2-Ethoxy-N-[5-(5-isopropyl-[1,3,4]thiadiazol-2-ylsulfamoyl)-indan-2-yl]-4-trifluoromethyl-benzamide
2-Ethoxy-N-[5-(5-isopropyl-[1,3,4]thiadiazol-2-ylsulfamoyl)-indan-2-yl]-4-trifluoromethyl-benzamide (Enantiomer 1)
2-Ethoxy-N-[5-(5-isopropyl-[1,3,4]thiadiazol-2-ylsulfamoyl)-indan-2-yl]-4-trifluoromethyl-benzamide (Enantiomer 2)
2-Ethoxy-4-trifluoromethyl-N-[5-(5-trifluoromethyl-[1,3,4]thiadiazol-2-ylsulfamoyl)-indan-2-yl]-benzamide
4-Methyl-2-(4-trifluormethyl-phenyl)-thiazol-5-carbonsäure-[5-(5-isopropyl-[1,3,4]thiadiazol-2-ylsulfamoyl)-indan-2-yl]-amid
4-Methyl-2-(4-trifluormethyl-phenyl)-thiazol-5-carbonsäure-[5-(5-cyclopropyl-[1,3,4]thiadiazol-2-ylsulfamoyl)-indan-2-yl]-amid
2-Ethoxy-N-[(S)-7-(5-isopropyl-[1,3,4]thiadiazol-2-ylsulfamoyl)-1,2,3,4-tetrahydro-naphthalen-2-yl]-4-trifluoromethyl-benzamide
2-Ethoxi-N-[(R)-7-(5-isopropyl-[1,3,4]thiadiazol-2-ylsulfamoyl)-1,2,3,4-tetrahydro-naphthalene-2-yl]-4-trifluoromethyl-benzamide
N-[5-Chloro-6-(5-isopropyl-[1,3,4]thiadiazol-2-ylsulfamoyl)-indan-2-yl]-2-ethoxy-4-trifluoromethyl-benzamide
2-Ethoxy-N-[5-(5-isopropyl-[1,3,4]thiadiazol-2-ylsulfamoyl)-6-methoxy-indan-2-yl]-4-trifluoromethyl-benzamide
3-Ethoxy-5-trifluoromethyl-thiophene-2-carboxylic acid [5-chloro-6-(5-isopropyl-[1,3,4]thiadiazol-2-ylsulfamoyl)-indan-2-yl]-amide
3-Ethoxy-5-trifluoromethyl-thiophene-2-carboxylic acid [5-(5-isopropyl-[1,3,4]thiadiazol-2-ylsulfamoyl)-6-methoxy-indan-2-yl]-amide
3-Ethoxy-5-trifluoromethyl-thiophene-2-carboxylic acid [5-(5-isopropyl-[1,3,4]thiadiazol-2-ylsulfamoyl)-indan-2-yl]-amide
2-Ethoxy-N-[2-(5-isopropyl-[1,3,4]thiadiazol-2-ylsulfamoyl)-6,7,8,9-tetrahydro-5H-benzocyclohepten-7-yl]-4-trifluoromethyl-benzamide
2-Chloro-N-[5-(5-isopropyl-[1,3,4]thiadiazol-2-ylsulfamoyl)-indan-2-yl]-5-trifluoromethyl-benzamide
4-Chloro-N-[5-(5-isopropyl-[1,3,4]thiadiazol-2-ylsulfamoyl)-indan-2-yl]-2-methyl-benzamide
2,3-Difluoro-N-[5-(5-isopropyl-[1,3,4]thiadiazol-2-ylsulfamoyl)-indan-2-yl]-4-trifluoromethyl-benzamide
2-Fluoro-N-[5-(5-isopropyl-[1,3,4]thiadiazol-2-ylsulfamoyl)-indan-2-yl]-4-trifluoromethyl-benzamide
4-Chloro-N-[5-(5-isopropyl-[1,3,4]thiadiazol-2-ylsulfamoyl)-indan-2-yl]-2-methoxi-benzamide
2,4-Dichloro-N-[5-(5-isopropyl-[1,3,4]thiadiazol-2-ylsulfamoyl)-indan-2-yl]-benzamide
2-Ethoxy-N-[5-fluoro-6-(5-isopropyl-[1,3,4]thiadiazol-2-ylsulfamoyl)-indan-2-yl]-4-trifluoromethyl-benzamide
2-Ethoxy-N-[5-(5-isopropyl-[1,3,4]thiadiazol-2-ylsulfamoyl)-1-methyl-indan-2-yl]-4-trifluoromethyl-benzamide 2-Ethoxy-N-[5-(5-isopropyl-[1,3,4]thiadiazol-2-ylsulfa-moyl)-6-(2,2,2-trifluoro-ethoxy)-indan-2-yl]-4-trifluoromethyl-benzamide N-[5-(5-Cyclopropyl-[1,3,4]thiadiazol-2-ylsulfamoyl)-indan-2-yl]-2-ethoxy-4-trifluoromethyl-benzamide 2-Ethoxy-N-[5-(5-phenyl-[1,3,4]thiadiazol-2-ylsulfamoyl)-indan-2-yl]-4-trifluoromethyl-benzamide 2-Ethoxy-N-[5-(5-cyclohexyl-[1,3,4]thiadiazol-2-ylsulfamoyl)-indan-2-yl]-4-trifluoromethyl-benzamide 3-Methoxy-pyridine-2-carboxylic acid [5-(5-isopropyl-[1,3,4]thiadiazol-2-ylsulfamoyl)-indan-2-yl]-amide.

This invention also encompasses all combinations of preferred aspects of the invention described herein.

As used herein, the term "alkyl" means saturated hydrocarbon residues which can be linear, i.e. straight-chain, or branched. If not otherwise defined alkyl has 1 to 8 carbon atoms. Examples of "—(C1-C8)-alkyl" are alkyl residues containing 1, 2, 3, 4, 5, 6, 7 or 8 carbon atoms are methyl, ethyl, propyl, butyl, pentyl, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. The term "—(C0-C8)-alkyl" is a hydrocarbon residue containing 1, 2, 3, 4, 5, 6, 7 or 8 carbon atoms, in which the term "—C0-alkyl" is a covalent bond. All these statements apply also to the term "alkylene".

All these statements also apply if an alkyl group occurs as a substituent on another residue, for example in an alkyloxy residue, an alkyloxycarbonyl residue or an arylalkyl residue.

If not otherwise defined, alkyl and alkylene are unsubstituted or mono-, di- or trisubstituted independently of one another by suitable groups such as, for example: F, Cl, Br, I, CF3, NO2, CN, COOH, CO—O—(C0-C4)alkylene-(C6-C10)aryl, CO—O—(C1-C4)alkyl, CO—O—(C0-C4)alkylene-(C3-C13)cycloalkyl, CO—O—(C0-C4)alkylene-(C3-C15)heterocycle, CO—N((C0-C4)alkylene-H)—(C0-C4)alkylene-(C6-C10)aryl, CO—N((C0-C4)alkylene-H)—(C0-C4)alkylene-H, CO—N((C0-C4)alkylene-H)—(C0-C4)alkylene-(C3-C13)cycloalkyl, CO—N((C0-C4)alkylene-H)—(C0-C4)alkylene-(C3-C15)heterocycle, (C0-C4)alkylene-(C3-C6)cycloalkyl, (C0-C4)alkylene-(C6-C10)aryl, (C0-C4)alkylene-(C3-C15)heterocycle, (C2-C6)alkenyl, (C2-C6)-alkynyl, O—(C0-C6)-alkyl, O—(C0-C4)alkylene-(C6-C10)aryl, O—(C0-C4)alkylene-(C3-C12)cycloalkyl, O—(C0-C4)alkylene-(C3-C15)heterocycle, O—CO—O—(C0-C4)alkylene-(C6-C10)aryl, O—CO—O—(C1-C4)alkyl, O—CO—O—(C0-C4)alkylene-(C3-C13)cycloalkyl, O—CO—O—(C0-C4)alkylene-(C3-C15)heterocycle, S—(C1-C4)alkyl, S—(C0-C4)alkylene-(C3-C13)cycloalkyl, S—(C0-C4)alkylene-(C6-C10)aryl, S—(C0-C4)alkylene-(C3-C15)heterocycle, SO—(C1-C4)alkyl, SO—(C0-C4)alkylene-(C3-C13)cycloalkyl, SO—(C0-C4)alkylene-(C6-C10)aryl, SO—(C0-C4)alkylene-(C3-C15)heterocycle, SO2-(C1-C4)alkyl, SO2-(C0-C4)alkylene-(C3-C13)cycloalkyl, SO2-(C0-C4)alkylene-(C6-C10)aryl, SO2-(C0-C4)alkylene-(C3-C15)heterocycle, SO2-N((C0-C4)alkylene-H)—(C0-C4)alkylene-(C6-C10)aryl, SO2-N((C0-C4)alkylene-H)—(C0-C4)alkylene-H, SO2-N((C0-C4)alkylene-H)—(C0-C4)alkylene-(C3-C13)cycloalkyl, SO2-N((C0-C4)alkylene-H)—(C0-C4)alkylene-(C3-C15)heterocycle where the aryl ring or heterocyclic ring is unsubstituted or mono- or disubstituted by F, Cl, Br, OH, CF3, NO2, CN, OCF3, O—(C1-C6)-alkyl, (C1-C6)-alkyl, N((C0-C4)-alkylene-H)—(C0-C4)-alkylene-H;

N((C0-C4)-alkylene-H)—(C0-C4)-alkylene-H, N((C0-C4)alkylene-H)—(C0-C4)alkylene-H)—(C1-C6)cycloalkyl, N((C0-C4)alkylene-H)—(C0-C4)alkylene-(C6-C12)-aryl, N((C0-C4)alkylene-H)—(C0-C4)alkylene-(C3-C15)heterocycle, N((C0-C4)alkylene-H)—CO—(C0-C4)alkylene-(C6-C12)-aryl, N((C0-C4)alkylene-H)—CO—(C0-C4)alkyl, N((C0-C4)alkylene-H)—CO—(C0-C4)alkylene-(C3-C13)cycloalkyl, N((C0-C4)alkylene-H)—CO—(C0-C4)alkylene-(C3-C15)heterocycle, N((C0-C4)alkylene-H)—CO—O—(C0-C4)alkylene-(C6-C12)-aryl, N((C0-C4)alkylene-H)—CO—O—(C0-C4)alkyl, N((C0-C4)alkylene-H)—CO—O—(C0-C4)alkylene-(C3-C13)cycloalkyl, N((C0-C4)alkylene-H)—CO—O—(C0-C4)alkylene-(C3-C15)heterocycle, N((C0-C4)alkylene-H)—CO—N((C0-C4)-alkylene-H)—(C0-C4)alkylene-(C6-C12)-aryl, N((C0-C4)alkylene-H)—CO—N((C0-C4)-alkylene-H)—(C0-C4)alkyl, N((C0-C4)alkylene-H)—CO—N((C0-C4)-alkylene-H)—(C0-C4)alkylene-(C3-C13)cycloalkyl, N((C0-C4)alkylene-H)—CO—N((C0-C4)-alkylene-H)—(C0-C4)alkylene-(C3-C15)heterocycle, where the aryl ring or heterocyclic ring is unsubstituted or mono- or disubstituted by F, Cl, Br, I, OH, CF3, NO2, CN, OCF3, O—(C1-C6)-alkyl, (C1-C6)-alkyl, N((C0-C4)-alkylene-H)—(C0-C4)-alkylene-H, SO2-CH3, COOH, COO—(C1-C6)-alkyl, SF5, CONH2.

The term "cycloalkyl" is to be understood to mean saturated hydrocarbon cycle containing from 3 to 13 carbon atoms in a mono- or bicyclic, fused, bridged or spirocyclic ring. Examples of (C3-C13)-cycloalkyl cyclic alkyl residues are cycloalkyl residues containing 3, 4, 5, 6, 7, 8, 9, 10, 11, 12 or 13 ring carbon atoms like cyclopropyl, cyclobutyl, cyclopentyl, cyclohexyl, cycloheptyl, cyclooctyl, cyclononyl, cyclodecyl, cycloundecyl or cyclododecyl. The term cycloalkyl also includes bicyclic groups in which any of the above cycloalkyl ring is fused to a benzene ring, for example indane and 1,2,3,4-tetrahydronaphthalene.

If not otherwise defined, cycloalkyl is unsubstituted or mono, di- or trisubstituted independently of one another by suitable groups such as, for example: F, Cl, Br, I, CF3, NO2, CN, COOH, CO—O—(C0-C4)alkylene-(C6-C10)aryl, CO—O—(C1-C4)alkyl, CO—O—(C0-C4)alkylene-(C3-C13)cycloalkyl, CO—O—(C0-C4)alkylene-(C3-C15)heterocycle, CO—N((C0-C4)alkylene-H)—(C1-C6)alkylene-H, CO—N((C0-C4)alkylene-H)—(C1-C6)cycloalkyl, CON((C0-C4)alkylene-H)—(C0-C4)alkylene-(C6-C12)-aryl, (C0-C4)alkylene-(C3-C6)cycloalkyl, (C3-C6)alkyl, (C2-C6)-alkenyl, (C2-C6)-alkynyl, (C0-C4)alkylene-(C6-C10)aryl, (C0-C4)alkylene-(C3-C15)heterocycle, O—(C0-C6)-alkyl, (C0-C4)alkylene-O—(C0-C4)alkyl, (C0-C4)alkylene-O—(C0-C4)alkylene-(C3-C13)cycloalkyl, (C0-C4)alkylene-O—(C0-C4)alkylene-(C6-C10)aryl, (C0-C4)alkylene-O—(C0-C4)alkylene-(C3-C15)heterocycle, O—CO—O—(C0-C4)alkylene-(C6-C10)aryl, O—CO—O—(C1-C4)alkyl, O—CO—O—(C0-C4)alkylene-(C3-C13)cycloalkyl, O—CO—O—(C0-C4)alkylene-(C3-C15)heterocycle, O—CO—N((C0-C4)alkylene-H)—(C0-C4)alkylene-(C6-C10)aryl, O—CO—N((C0-C4)alkylene-H)—(C0-C4)alkylene-H, O—CO—N((C0-C4)alkylene-H)—(C0-C4)alkylene-(C3-C13)cycloalkyl, O—CO—N((C0-C4)alkylene-H)—(C0-C4)alkylene-(C3-C15)heterocycle, S—(C1-C4)alkyl, S—(C0-C4)alkylene-(C3-C13)cycloalkyl, S—(C0-C4)alkylene-(C6-C10)aryl, S—(C0-C4)alkylene-(C3-C15)heterocycle, SO—(C1-C4)alkyl, SO—(C0-C4)alkylene-(C3-C13)cycloalkyl, SO—(C0-C4)alkylene-(C6-C10)aryl, SO—(C0-C4)alkylene-(C3-C15)heterocycle, SO2-(C1-C4)alkyl, SO2-(C0-C4)alkylene-(C3-C13)cycloalkyl, SO2-(C0-C4)alkylene-(C6-C10)aryl, SO2-(C0-C4)alkylene-(C3-C15)heterocycle, SO2-N((C0-C4)alkylene-H)—(C0-C4)alkylene-(C6-C10)aryl, SO2-N((C0-C4)alkylene-H)—(C0-C4)alkylene-H, SO2-N((C0-C4)alkylene-H)—(C0-C4)alkylene-(C3-C13)cycloalkyl, SO2-N((C0-C4)alkylene-H)—(C0-C4)alkylene-(C3-C15)heterocycle, where the aryl ring or heterocyclic ring is unsubstituted or mono- or disubstituted by F, Cl, Br, OH, CF3, NO2, CN, OCF3, O—(C1-C6)-alkyl, (C1-C6)-alkyl, N((C0-C4)-alkylene-H)—(C0-C4)-alkylene-H; N((C0-C4)-alkylene-H)—(C0-C4)-alkylene-H, N((C0-C4)alkylene-H)—(C0-C4)alkylene-H)—(C1-C6)cycloalkyl, N((C0-C4)alkylene-H)—(C0-C4)alkylene-(C6-C12)-aryl, N((C0-C4)alkylene-H)—(C0-C4)alkylene-(C3-C15)heterocycle, N((C0-C4)alkylene-H)—CO—(C0-C4)alkylene-(C6-C12)-aryl, N((C0-C4)alkylene-H)—CO—(C0-C4)alkyl, N((C0-C4)alkylene-H)—CO—(C0-C4)alkylene-(C3-C13)cycloalkyl, N((C0-C4)alkylene-H)—CO—(C0-C4)alkylene-(C3-C15)heterocycle, N((C0-C4)alkylene-H)—CO—O—(C0-C4)alkylene-(C6-C12)-aryl, N((C0-C4)alkylene-H)—CO—O—(C0-C4)alkyl, N((C0-C4)alkylene-H)—CO—O—(C0-C4)alkylene-(C3-C13)cycloalkyl, N((C0-C4)alkylene-H)—CO—O—(C0-C4)alkylene-(C3-C15) heterocycle, N((C0-C4)alkylene-H)—CO—N((C0-C4)-alkylene-H)—(C0-C4)alkylene-(C6-C12)-aryl, N((C0-C4)alkylene-H)—CO—N((C0-C4)-alkylene-H)—(C0-C4)alkyl, N((C0-C4)alkylene-H)—CO—N((C0-C4)-alkylene-H)—(C0-C4)alkylene-(C3-C13)cycloalkyl, N((C0-C4)alkylene-H)—CO—N((C0-C4)-alkylene-H)—(C0-C4)alkylene-(C3-C15)heterocycle, where the aryl or heterocyclic ring is unsubstituted or mono- or disubstituted by F, Cl, Br, I, OH, CF3, NO2, CN, OCF3, O—(C1-C6)-alkyl, (C1-C6)-alkyl, N((C0-C4)-alkylene-H)—(C0-C4)-alkylene-H, SO2-CH3, COOH, COO—(C1-C6)-alkyl, SF5, CONH2.

The term "aryl" means an aromatic hydrocarbon ring containing from 6 to 14 carbon atoms in a mono- or bicyclic ring. Examples of (C6-C14)-aryl rings are phenyl, naphthyl, for example 1-naphthyl and 2-naphthyl, biphenyl, for example 2-biphenyl, 3-biphenyl and 4-biphenyl, anthryl or fluorenyl. Biphenyl rings, naphthyl ring and, in particular, phenyl ring are further embodiments of aryl ring.

The term "heterocycle" means a saturated (heterocycloalkyl), partly unsaturated (heterocycloalkenyl) or unsaturated (heteroaryl)hydrocarbon rings containing from 3 to 15 carbon atoms in a mono- or bicyclic, fused, bridged or spirocyclic ring in which 1 to 5 carbon atoms of the 3 to 15 ring carbon atoms are replaced by heteroatoms such as nitrogen, oxygen or sulfur in which further the heteroatoms can be oxidized, for example N=O, S=O, SO2. Examples of heterocycles are acridinyl, azaindole (1H-pyrrolopyridinyl), azabenzimidazolyl, azaspirodecanyl, azepinyl, azetidinyl, aziridinyl, benzimidazolyl, benzofuranyl, dihydrobenzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The heterocyclic rings are unsubstituted or mono-, di- or trisubstituted by suitable groups such as, for example: F, Cl, Br, I, CF3, NO2, CN, COOH, CO—O—(C0-C4)alkylene-(C6-C10)aryl, CO—O—(C1-C4)alkyl, CO—O—(C0-C4)alkylene-(C3-C13)cycloalkyl, CO—O—(C0-C4)alkylene-(C3-C15)heterocycle, CO—N((C0-C4)alkylene-H)—(C1-C6)alkylene-H, CO—N((C0-C4)alkylene-H)—(C1-C6)cycloalkyl, CON((C0-C4)alkylene-H)—(C0-C4)alkylene-(C6-C12)-aryl, (C0-C4)alkylene-(C3-C6)cycloalkyl, (C3-C6)alkyl, (C2-C6)-alkenyl, (C2-C6)-alkynyl, (C0-C4)alkylene-(C6-C10)aryl, (C0-C4)alkylene-(C3-C15) heterocycle, O—(C0-C6)-alkyl, (C0-C4)alkylene-O—(C0-C4)alkyl, (C0-C4)alkylene-O—(C0-C4)alkylene-(C3-C13)cycloalkyl, (C0-C4)alkylene-O—(C0-C4)alkylene-(C6-C10)aryl, (C0-C4)alkylene-O—(C0-C4)alkylene-(C3-C15)heterocycle, O—CO—O—(C0-C4)alkylene-(C6-C10)aryl, O—CO—O—(C1-C4)alkyl, O—CO—O—(C0-C4)alkylene-(C3-C13)cycloalkyl, O—CO—O—(C0-C4)alkylene-(C3-C15)heterocycle, O—CO—N((C0-C4)alkylene-H)—(C0-C4)alkylene-(C6-C10)aryl, O—CO—N((C0-C4)alkylene-H)—(C0-C4)alkylene-H, O—CO—N((C0-C4)alkylene-H)—(C0-C4)alkylene-(C3-C13)cycloalkyl, O—CO—N((C0-C4)alkylene-H)—(C0-C4)alkylene-(C3-C15)heterocycle, S—(C1-C4)alkyl, S—(C0-C4)alkylene-(C3-C13)cycloalkyl, S—(C0-C4)alkylene-(C6-C10)aryl, S—(C0-C4)alkylene-(C3-C15)heterocycle, SO—(C1-C4)alkyl, SO—(C0-C4)alkylene-(C3-C13)cycloalkyl, SO—(C0-C4)alkylene-(C6-C10)aryl, SO—(C0-C4)alkylene-(C3-C15)heterocycle, SO2-(C1-C4)alkyl, SO2-(C0-C4)alkylene-(C3-C13)cycloalkyl, SO2-(C0-C4)alkylene-(C6-C10)aryl, SO2-(C0-C4)alkylene-(C3-C15)heterocycle, SO2-N((C0-C4)alkylene-H)—(C0-C4)alkylene-(C6-C10)aryl, SO2-N((C0-C4)alkylene-H)—(C0-C4)alkylene-H, SO2-N((C0-C4)alkylene-H)—(C0-C4)alkylene-(C3-C13)cycloalkyl, SO2-N((C0-C4)alkylene-H)—(C0-C4)alkylene-(C3-C15) heterocycle, where the aryl ring or heterocyclic ring is unsubstituted or mono- or disubstituted by F, Cl, Br, OH, CF3, NO2, CN, OCF3, O—(C1-C6)-alkyl, (C1-C6)-alkyl, N((C0-C4)-alkylene-H)—(C0-C4)-alkylene-H;

N((C0-C4)-alkylene-H)—(C0-C4)-alkylene-H, N((C0-C4)alkylene-H)—(C0-C4)alkylene-H)—(C1-C6)cycloalkyl, N((C0-C4)alkylene-H)—(C0-C4)alkylene-(C6-C12)-aryl, N((C0-C4)alkylene-H)—(C0-C4)alkylene-(C3-C15)heterocycle, N((C0-C4)alkylene-H)—CO—(C0-C4)alkylene-(C6-C12)-aryl, N((C0-C4)alkylene-H)—CO—(C0-C4)alkyl, N((C0-C4)alkylene-H)—CO—(C0-C4)alkylene-(C3-C13)cycloalkyl, N((C0-C4)alkylene-H)—CO—(C0-C4)alkylene-(C3-C15)heterocycle, N((C0-C4)alkylene-H)—CO—O—(C0-C4)alkylene-(C6-C12)-aryl, N((C0-C4)alkylene-H)—CO—O—(C0-C4)alkyl, N((C0-C4)alkylene-H)—CO—O—(C0-C4)alkylene-(C3-C13)cycloalkyl, N((C0-C4)alkylene-H)—CO—O—(C0-C4)alkylene-(C3-C15) heterocycle, N((C0-C4)alkylene-H)—CO—N((C0-C4)- alkylene-H)—(C0-C4)alkylene-(C6-C12)-aryl, N((C0-C4)alkylene-H)—CO—N((C0-C4)-alkylene-H)—(C0-C4)alkyl, N((C0-C4)alkylene-H)—CO—N((C0-C4)-alkylene-H)—(C0-C4)alkylene-(C3-C13)cycloalkyl, N((C0-C4)alkylene-H)—CO—N((C0-C4)-alkylene-H)—(C0-C4)alkylene-(C3-C15)heterocycle, where the aryl or heterocyclic ring is unsubstituted or mono- or disubstituted by F, Cl, Br, I, OH, CF3, NO2, CN, OCF3, O—(C1-C6)-alkyl, (C1-C6)-alkyl, N((C0-C4)-alkylene-H)—(C0-C4)-alkylene-H, SO2-CH3, COOH, COO—(C1-C6)-alkyl, SF5, CONH2.

The term "oxo-residue" or "=O" refers to residues such as carbonyl (—CO—), nitroso (—N=O), sulfinyl (—SO— or sulfonyl (—SO$_2$—).

Halogen is a fluorine, chlorine, bromine or iodine.

Optically active carbon atoms present in the compounds of formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers by chromatography, for example. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

The compounds of the formula I may exist in the form of their racemates, racemic mixtures, pure enantiomers, diastereomers and mixtures of diastereomers as well in their tautomeric forms. The present invention encompasses all these isomeric and tautomeric forms of the compounds of the formula I. These isomeric forms can be obtained by known methods even if not specifically described in some cases.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

I. Methods of Use

This invention relates further to the use of compounds of the formula I and their pharmaceutical compositions as peroxisome proliferator activated receptor (PPAR) ligands. The PPAR ligands of the invention are useful in the modulation of PPAR activity since they are transcription factors which can be activated by ligands and belong to the class of nuclear hormone receptors. As discussed above, they are encoded by different genes (Peroxisome proliferator-activated receptor (PPAR): structure, mechanisms of activation and have diverse functions: Motojima K., Cell Struct Funct., 1993, 18(5), 267-77).

Compounds of this type are particularly suitable for the treatment and/or prevention of:

1. Disorders of fatty acid metabolism and glucose utilization disorders.
   Disorders in which insulin resistance is involved
2. Diabetes mellitus, especially type-2 diabetes, including the prevention of the sequelae associated therewith.
   Particular aspects in this connection are
   hyperglycemia,
   improvement in insulin resistance,
   improvement in glucose tolerance,
   protection of the pancreatic β cells
   prevention of macro- and microvascular disorders
3. Dyslipidemias and their sequelae such as atherosclerosis, coronary heart disease, cerebrovascular disorders etc, especially those (but not restricted thereto) which are characterized by one or more of the following factors:
   high plasma triglyceride concentrations, high postprandial plasma triglyceride concentrations,
   low HDL cholesterol concentrations
   low ApoA lipoprotein concentrations
   high LDL cholesterol concentrations
   small dense LDL cholesterol particles
   high ApoB lipoprotein concentrations
4. Various other conditions which may be associated with the metabolic syndrome, such as:
   obesity (excess weight), including central obesity
   thromboses, hypercoagulable and prothrombotic states (arterial and venous)
   high blood pressure heart failure such as, for example (but not restricted thereto), following myocardial infarction, hypertensive heart disease or cardiomyopathy 5. Disorders or conditions in which inflammatory reactions are involved:
   atherosclerosis such as, for example (but not restricted thereto), coronary sclerosis including angina pectoris or myocardial infarction, stroke
   vascular restenosis or reocclusion
   chronic inflammatory bowel diseases such as, for example, Crohn's disease and ulcerative colitis
   asthma
   lupus erythematosus (LE) or inflammatory rheumatic disorders such as, for example, rheumatoid arthritis
   other inflammatory states 6. Disorders of cell cycle or cell differentiation processes:
   adipose cell tumors
   lipomatous carcinomas such as, for example, liposarcomas
   solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
   acute and chronic myeloproliferative disorders and lymphomas
   angiogenesis 7. Demyelinating and other neurodegenerative disorders of the central and peripheral nervous systems including:
   Alzheimer's disease
   multiple sclerosis
   Parkinson's disease
   adrenoleukodystrophy (ALD)
   adrenomyeloneuropathy
   AIDS-vacuolar myelopathy
   HTLV-associated myelopathy
   Leber's hereditary optic atrophy
   progressive multifocal leukoencephalopathy (PML)
   subacute sclerosing panencephalitis
   Guillian-Barre syndrome
   tropical spastic paraparesis
   acute disseminated encephalomyelitis (ADEM)
   acute viral encephalitis
   acute transverse myelitis
   spinal cord and brain trauma
   Charcot-Marie-Tooth disease 8. Skin disorders and/or disorders of wound healing processes:
   erythemato-squamous dermatoses such as, for example, psoriasis
   acne vulgaris
   other skin disorders and dermatological conditions which are modulated by PPAR
   eczemas and neurodermitis
   dermatitis such as, for example, seborrheic dermatitis or photodermatitis
   keratitis and keratoses such as, for example, seborrheic keratoses, senile keratoses, actinic keratosis, photo-induced keratoses or keratosis follicularis
   keloids and keloid prophylaxis
   warts, including condylomata or condylomata acuminata
   human papilloma viral (HPV) infections such as, for example, venereal papillomata, viral warts such as, for example, molluscum contagiosum, leukoplakia
   papular dermatoses such as, for example, Lichen planus
   skin cancer such as, for example, basal-cell carcinomas, melanomas or cutaneous T-cell lymphomas
   localized benign epidermal tumors such as, for example, keratoderma, epidermal naevi
   chilblains
   wound healing 9. Other disorders
   high blood pressure
   pancreatitis
   syndrome X
   polycystic ovary syndrome (PCOS)
   asthma
   osteoarthritis
   lupus erythematosus (LE) or inflammatory rheumatic disorders such as, for example, rheumatoid arthritis
   vasculitis
   wasting (cachexia)
   gout
   ischemia/reperfusion syndrome
   acute respiratory distress syndrome (ARDS)

II. Pharmaceutical Formulations

The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on metabolic disorders. They beneficially influence lipid and sugar metabolism, in particular they lower the triglyceride level and are suitable for the prevention and treatment of type II diabetes and atherioscierosis and the diverse sequalae thereof.

Pharmaceutical Combinations with Other Actives

The compounds of the invention can be administered alone or in combination with one or more additional, pharmacologically active substances. In particular, the compounds of the invention can be administered in combination with active ingredients having a similar pharmacological action. For example, they can be administered in combination with active ingredients that are therapeutically effective in the treatment of metabolic disturbances and the disorders frequently associated therewith. Examples of such secondary pharmaceutical actives are:

1. Pharmaceutical active compounds that lower blood glucose.
2. Pharmaceutical active compounds for the treatment of dyslipidemias.
3. Pharmaceutical active compounds for the treatment of atherosclerosis.
4. Anti-obesity agents.
5. Anti-inflammatory active ingredients.
6. Anti-cancer agents for the treatment of tumors.
7. Anti-thrombotic actives.
8. Cardiovascular agents for the treatment of blood pressure and heart failure.
9. Neurological actives for the treatment of the central nervous system.
10. Anti-diabetic agents for the treatment and of diabetes and its' complications. Pharmaceutical actives for the treatment of drug, nicotine and alcohol addiction
11. Analgesics These compounds can be combined with the compounds of the present invention of formula I in particular for the generation of a synergistic enhancement of activity. Administration of the active ingredient combination can take place either by separate administration of the active ingredients to the patient (adjunct therapy) or in the form of combination products in which a plurality of active ingredients are present in one pharmaceutical preparation.

Preferable secondary pharmaceutical actives for the combination preparations are:

All anti-diabetics mentioned in the Rote Liste 2006, Chapter 12; all slimming agents/appetite suppressants mentioned in the Rote Liste 2006, Chapter 1; all lipid-lowering agents mentioned in the Rote Liste 2006, Chapter 58. They can be combined with the compound of the formula I according to the invention in particular for a synergistic enhancement of activity. The active compound combination can be administered either by separate administration of the active compounds to the patient or in the form of combination preparations in which a plurality of active compounds are present in a pharmaceutical preparation. Most of the active compounds listed below are disclosed in USP Dictionary of USAN and International Drug Names, US Pharmacopeia, Rockville 2001.

Anti-diabetics include insulin and insulin derivatives, such as, for example, Lantus® (see www.lantus.com) or HMR 1964 or those described in WO2005005477 (Novo Nordisk), fast-acting insulins (see U.S. Pat. No. 6,221,633), inhalable insulins, such as, for example, Exubera® or oral insulins, such as, for example, IN-105 (Nobex) or Oral-lyn™ (Generex Biotechnology), GLP-1 derivatives, such as, for example, Exenatide, Liraglutide or those disclosed in WO 98/08871 or WO2005027978 by Novo Nordisk A/S, in WO 01/04156 by Zealand or in WO 00/34331 by Beaufour-Ipsen, pramlintide acetate (Symlin; Amylin Pharmaceuticals), and also orally effective hypoglycemic active ingredients.

The active compounds preferably include
sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase,
modulators of the glucose transporter 4 (GLUT4),
inhibitors of glutamine:fructose-6-phosphate amidotransferase (GFAT),
GLP-1 agonists,
potassium channel openers, such as, for example, those disclosed in WO 97/26265 and WO 99/03861 by Novo Nordisk A/S,
inhibitors of dipeptidylpeptidase IV (DPP-IV),
insulin sensitizers,
inhibitors of liver enzymes involved in the stimulation of gluconeogenesis and/or glycogenolysis,
modulators of glucose uptake, glucose transport and glucose back resorption,
inhibitors of 11β-HSD1,
inhibitors of protein tyrosine phosphatase 1B (PTP1B),
modulators of the sodium/glucose cotransporter 1 or 2 (SGLT1, SGLT2),
compounds which alter lipid metabolism, such as antihyperlipidemic active ingredients and antilipidemic active ingredients,
compounds which reduce food intake or food absorption,
compounds which increase thermogenesis,
PPAR and RXR modulators and
active ingredients which act on the ATP-dependent potassium channel of the beta cells.

In one embodiment of the invention, the compound of formula I is administered in combination with a HMGCoA reductase inhibitor, such as simvastatin, fluvastatin, pravastatin, lovastatin, atorvastatin, cerivastatin, rosuvastatin or L-659699.

In a second embodiment of the invention, the compound of formula I is administered in combination with a cholesterol resorption inhibitor, such as, for example, ezetimibe, tiqueside, pamaqueside, FM-VP4 (sitostanol/campesterol ascorbyl phosphate; Forbes Medi-Tech, WO2005042692), MD-0727 (Microbia Inc., WO2005021497) or with compounds as described in WO2002066464 (Kotobuki Pharmaceutical Co. Ltd.), WO2005062824 (Merck & Co.) or WO2005061451 and WO2005061452 (AstraZeneca AB).

In a third embodiment of the invention, the compound of formula I is administered in combination with a PPAR gamma agonist, such as, for example, rosiglitazone, pioglitazone, JTT-501, GI 262570, R-483 or CS-011 (rivoglitazone).

In a fourth embodiment of the invention, the compound of formula I is administered in combination with a PPAR alpha agonist, such as, for example, GW9578, GW-590735, K-111, LY-674, KRP-101 or DRF-10945.

In another embodiment of the invention, the compound of the formula I is administered in combination with a mixed PPAR alpha/gamma agonist, such as, for example, muraglitazar, tesaglitazar, naveglitazar, LY-510929, ONO-5129, E-3030 or as described in WO00/64888, WO00/64876, WO03/020269, WO2004075891, WO2004076402, WO2004075815, WO2004076447, WO2004076428, WO2004076401, WO2004076426, WO2004076427, WO2006018118, WO2006018115, and WO2006018116 or in J. P. Berger et al., TRENDS in Pharmacological Sciences 28(5), 244-251, 2005.

In one embodiment of the invention, the compound of the formula I is administered in combination with a PPAR delta agonist, such as, for example, GW-501516 or as described in WO2005097762, WO2005097786, WO2005097763, and WO2006029699.

In another embodiment of the invention, the compound of the formula I is administered in combination with metaglidasen or with MBX-2044 or other partial PPAR gamma agonists/antagonists.

In one embodiment of the invention, the compound of the formula I is administered in combination with a fibrate, such as, for example, fenofibrate, clofibrate or bezafibrate.

In another embodiment of the invention, the compound of the formula I is administered in combination with an MTP inhibitor, such as, for example, implitapide, BMS-201038, R-103757 or those described in WO2005085226.

In one embodiment of the invention, the compound of the formula I is administered in combination with a CETP inhibitor, such as, for example, torcetrapib or JTT-705.

In another embodiment of the invention, the compound of the formula I is administered in combination with a bile acid resorption inhibitor (see, for example, U.S. Pat. No. 6,245,744, U.S. Pat. No. 6,221,897 or WO00/61568), such as, for example, HMR 1741 or those described in DE 10 2005 033099.1 and DE 10 2005 033100.9.

In one embodiment of the invention, the compound of the formula I is administered in combination with a polymeric bile acid adsorber, such as, for example, cholestyramine or colesevelam.

In another embodiment of the invention, the compound of the formula I is administered in combination with an LDL receptor inducer (see U.S. Pat. No. 6,342,512), such as, for example, HMR1171, HMR1586 or those described in WO2005097738.

In one embodiment, the compound of formula I is administered in combination with Omacor® (omega-3 fatty acids; highly concentrated ethyl esters of eicosapentaenoic acid and docosahexaenoic acid).

In another embodiment of the invention, the compound of formula I is administered in combination with an ACAT inhibitor, such as, for example, avasimibe.

In one embodiment of the invention, the compound of formula I is administered in combination with an antioxidant, such as, for example, OPC-14117, probucol, tocopherol, ascorbic acid, β-carotene or selenium.

In another embodiment of the invention, the compound of formula I is administered in combination with a vitamin, such as, for example, vitamin B6 or vitamin B12.

In one embodiment of the invention, the compound of formula I is administered in combination with a lipoprotein lipase modulator, such as, for example, ibrolipim (NO-1886).

In another embodiment of the invention, the compound of formula I is administered in combination with an ATP-citrate lyase inhibitor, such as, for example, SB-204990.

In one embodiment of the invention, the compound of formula I is administered in combination with a squalene synthetase inhibitor, such as, for example, BMS-188494 or as described in WO2005077907.

In another embodiment of the invention, the compound of formula I is administered in combination with a lipoprotein (a) antagonist, such as, for example, gemcabene (CI-1027).

In one embodiment of the invention, the compound of formula I is administered in combination with an HM74A receptor agonists, such as, for example, nicotinic acid.

In another embodiment of the invention, the compound of formula I is administered in combination with a lipase inhibitor, such as, for example, orlistat or cetilistat (ATL-962).

In one embodiment of the invention, the compound of formula I is administered in combination with insulin.

In one embodiment of the invention, the compound of formula I is administered in combination with a sulfonylurea, such as, for example, tolbutamide, glibenclamide, glipizide or glimepiride.

In one embodiment of the invention, the compound of formula I is administered in combination with a biguanide, such as, for example, metformin.

In another embodiment of the invention, the compound of formula I is administered in combination with a meglitinide, such as, for example, repaglinide or nateglinide.

In another embodiment of the invention, the compound of the formula I is administered in combination with a thiazolidinedione, such as, for example, troglitazone, ciglitazone, pioglitazone, rosiglitazone or the compounds disclosed in WO 97/41097 by Dr. Reddy's Research Foundation, in particular 5-[[4-[(3,4-dihydro-3-methyl-4-oxo-2-quinazolinyl-methoxy]phenyl]methyl]-2,4-thiazolidinedione.

In one embodiment of the invention, the compound of formula I is administered in combination with an α-glucosidase inhibitor, such as, for example, miglitol or acarbose. In another embodiment of the invention, the compound of formula I is administered in combination with an active ingredient which acts on the ATP-dependent potassium channel of the beta cells, such as, for example, tolbutamide, glibenclamide, glipizide, glimepiride or repaglinide.

In one embodiment of the invention, the compound of formula I is administered in combination with more than one of the compounds mentioned above, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In another embodiment of the invention, the compound of formula I is administered in combination with an inhibitor of glycogen phosphorylase, such as, for example, PSN-357 or FR-258900 or those described in WO2003084922, WO2004007455, WO2005073229-31 or WO2005067932.

In one embodiment of the invention, the compound of formula I is administered in combination with glucagon receptor antagonists, such as, for example, A-770077, NNC-25-2504 or such as in WO2004100875 or WO2005065680.

In another embodiment of the invention, the compound of formula I is administered in combination with activators of glucokinase, such as, for example, RO-4389620, LY-2121260 (WO2004063179), PSN-105, PSN-110, GKA-50 or those described, for example, by Prosidion in WO2004072031, WO2004072066, WO 05103021 or WO 06016178, by Roche in WO 00058293, WO 00183465, WO 00183478, WO 00185706, WO 00185707, WO 01044216, GB 02385328, WO 02008209, WO 02014312, WO 0246173, WO 0248106, DE 10259786, WO 03095438, U.S. Pat. No. 4,067,939 or WO 04052869, by Novo Nordisk in EP 1532980, WO 03055482, WO 04002481, WO 05049019, WO 05066145 or WO 05123132, by Merck/Banyu in WO 03080585, WO03097824, WO 04081001, WO 05063738 or WO 05090332, by Eli Lilly in WO 04063194, or by Astra Zeneca in WO 01020327, WO 03000262, WO 03000267, WO 03015774, WO 04045614, WO 04046139, WO 05044801, WO 05054200, WO 05054233, WO 05056530, WO 05080359, WO 05080360 or WO 05121110.

In one embodiment of the invention, the compound of formula I is administered in combination with an inhibitor of gluconeogenesis, such as, for example, FR-225654.

In another embodiment of the invention, the compound of formula I is administered in combination with inhibitors of fructose-1,6-bisphosphatase (FBPase), such as, for example, CS-917.

In one embodiment of the invention, the compound of the formula I is administered in combination with modulators of the glucose transporter 4 (GLUT4), such as, for example, KST-48 (D.-O. Lee et al.: Arzneim.-Forsch. Drug Res. 54 (12), 835 (2004)).

In one embodiment of the invention, the compound of formula I is administered in combination with inhibitors of glutamine:fructose-6-phosphate amidotransferase (GFAT), as described, for example, in WO2004101528.

In another embodiment of the invention, the compound of formula I is administered in combination with inhibitors of dipeptidylpeptidase IV (DPP-IV), such as, for example, vildagliptin (LAF-237), sitagliptin (MK-0431), saxagliptin ((BMS-477118), GSK-823093, PSN-9301, SYR-322, SYR-619, TA-6666, TS-021, GRC-8200, GW-825964X or as described in WO2003074500, WO2003106456, WO200450658, WO2005058901, WO2005012312, WO2005/012308, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment of the invention, the compound of formula I is administered in combination with inhibitors of 11-beta-hydroxysteroid dehydrogenase-1 (11β-HSD1), such as, for example, BVT-2733 or those described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004065351, WO2004089367, WO2004089380, WO2004089470-71, WO2004089896, WO2005016877 or WO2005097759.

In another embodiment of the invention, the compound of formula I is administered in combination with inhibitors of protein tyrosine phosphatase 1B (PTP1B), as described, for example, in WO200119830-31, WO200117516, WO2004506446, WO2005012295, PCT/EP2005/005311, PCT/EP2005/005321, PCT/EP2005/007151, PCT/EP2005/ or DE 10 2004 060542.4.

In one embodiment of the invention, the compound of formula I is administered in combination with modulators of the sodium/glucose cotransporter 1 or 2 (SGLT1, SGLT2), such as, for example, KGA-2727, T-1095 and SGL-0010 or as described, for example, in WO2004007517, WO200452903, WO200452902, WO2005121161, WO2005085237, JP2004359630 or by A. L. Handlon in Expert Opin. Ther. Patents (2005) 15(11), 1531-1540.

In another embodiment of the invention, the compound of formula I is administered in combination with inhibitors of hormone-sensitive lipase (HSL), such as those described, for example, in WO01/17981, WO01/66531, WO2004035550, WO2005073199 or WO03/051842.

In one embodiment of the invention, the compound of formula I is administered in combination with inhibitors of acetyl-CoA carboxylase (ACC) such as those described, for example, in WO199946262, WO200372197, WO2003072197 or WO2005044814.

In one embodiment of the invention, the compound of formula I is administered in combination with an inhibitor of phosphoenolpyruvate carboxykinase (PEPCK), such as those described, for example, in WO2004074288.

In another embodiment of the invention, the compound of formula I is administered in combination with an inhibitor of glycogen synthase kinase-3 beta (GSK-3 beta), such as those described, for example, in US2005222220, WO2004046117, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727 or WO2004046117.

In another embodiment of the invention, the compound of the formula I is administered in combination with an inhibitor of protein kinase C beta (PKC beta), such as, for example, ruboxistaurin.

In one embodiment of the invention, the compound of the formula I is administered in combination with an endothelin-A receptor antagonist, such as, for example, avosentan (SPP-301).

In another embodiment of the invention, the compound of formula I is administered in combination with inhibitors of "I-kappaB kinase" (IKK inhibitors), such as those described, for example, in WO2001000610, WO2001030774, WO2004022553 or WO2005097129.

In one embodiment of the invention, the compound of formula I is administered in combination with modulators of the glucocorticoid receptor as described, for example, in WO2005090336.

In a further embodiment of the invention, the compound of formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists such as, for example, {4-[(4-aminoquinazolin-2-ylamino)methyl]-cyclohexylmethyl}naphthalene-1-sulfonamide hydrochloride (CGP 71683A);

peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those described in WO2005080424; cannabinoid receptor 1 antagonists, such as, for example, rimonabant, SR147778 or those described, for example, in EP 0656354, WO 00/15609, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509 or WO2005077897;

MC4 agonists (for example [2-(3a-benzyl-2-methyl-3-oxo-2,3,3a,4,6,7-hexahydro-pyrazolo[4,3-c]pyridin-5-yl)-1-(4-chlorophenyl)-2-oxoethyl]-1-amino-1,2,3,4-tetrahydro-naphthalene-2-carboxamide; (WO 01/91752)) or LB53280, LB53279, LB53278 or THIQ, MB243, RY764, CHIR-785, PT-141 or those described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, EP1538159, WO2004072076, WO2004072077 or WO2006024390;

orexin receptor antagonists (for example 1-(2-methylbenzoxazol-6-yl)-3-[1,5]naphthyridin-4-ylurea hydrochloride (SB-334867-A) or those described, for example, in WO200196302, WO200185693, WO2004085403 or WO2005075458);

histamine H3 receptor agonists (for example 3-cyclohexyl-1-(4,4-dimethyl-1,4,6,7-tetrahydroimidazo[4,5-c]pyridin-5-yl)-propan-1-one oxalic acid salt (WO 00/63208) or those described in WO200064884, WO2005082893);

CRF antagonists (for example [2-methyl-9-(2,4,6-trimethylphenyl)-9H-1,3,9-triazafluoren-4-yl]dipropylamine (WO 00/66585));

CRF BP antagonists (for example urocortin);

urocortin agonists;

β3 agonists (such as, for example, 1-(4-chloro-3-methanesulfonylmethylphenyl)-2-[2-(2,3-dimethyl-1H-indol-6-yloxy)ethylamino]ethanol hydrochloride (WO 01/83451));

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or those compounds described in WO2003/15769, WO2005085200, WO2005019240, WO2004011438, WO2004012648, WO2003015769, WO2004072025, WO2005070898, WO2005070925, WO2006018280, WO2006018279, WO2004039780, WO2003033476, WO2002006245, WO2002002744, WO2003004027 or FR2868780);

CCK-A agonists (such as, for example, {2-[4-(4-chloro-2,5-dimethoxyphenyl)-5-(2-cyclohexylethyl)-thiazol-2-ylcarbamoyl]-5,7-dimethylindol-1-yl}acetic acid trifluoroacetic acid salt (WO 99/15525), SR-146131 (WO 0244150) or SSR-125180);

serotonin reuptake inhibitors (for example dexfenfluramine);

mixed serotonin- and noradrenergic compounds (for example WO 00/71549);

5-HT receptor agonists, for example 1-(3-ethylbenzofuran-7-yl)piperazine oxalic acid salt (WO 01/09111);

5-HT2C receptor agonists (such as, for example, APD-356, BVT-933 or those described in WO200077010, WO20077001-02, WO2005019180, WO2003064423, WO200242304 or WO2005082859);

5-HT6 receptor antagonists, such as described, for example, in WO2005058858;

bombesin receptor agonists (BRS-3 agonists);

galanin receptor antagonists;

growth hormone (for example human growth hormone or AOD-9604);

growth hormone releasing compounds (tert-butyl 6-benzyloxy-1-(2-diisopropylamino-ethylcarbamoyl)-3,4-dihydro-1H-isoquinoline-2-carboxylate (WO 01/85695));

growth hormone secretagog receptor antagonists (ghrelin antagonists) such as, for example, A-778193 or those described in WO2005030734;

TRH agonists (see, for example, EP 0 462 884);

uncoupling protein 2 or 3 modulators;

leptin agonists (see for example Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881);
DA agonists (bromocriptine or Doprexin);
lipase/amylase inhibitors (as described, for example, in WO 00/40569);
inhibitors of diacylglycerol O-acyltransferases (DGATs) such as described, for example, in US2004/0224997, WO2004094618, WO200058491, WO2005044250, WO2005072740, JP2005206492 or WO2005013907;
inhibitors of fatty acid synthase (FAS) such as, for example, C75 or those described in WO2004005277;
oxyntomodulin;
oleoyl-estrone or thyroid hormone receptor agonists, such as, for example, KB-2115 or those described in WO20058279, WO200172692, WO200194293, WO2003084915, WO2004018421 or WO2005092316.

In one embodiment of the invention, the further active ingredient is leptin; see for example "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment of the invention, the further active ingredient is dexamphetamine or amphetamine.

In one embodiment of the invention, the further active ingredient is fenfluramine or dexfenfluramine.

In another embodiment of the invention, the further active ingredient is sibutramine.

In one embodiment of the invention, the further active ingredient is mazindol or phentermine.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compound of the formula I is administered in combination with PDE (phosphodiesterase) inhibitors, as described, for example, in WO2003/077949 or WO2005012485.

In one embodiment of the invention, the compound of the formula I is administered in combination with NAR-1 (nicotinic acid receptor) agonists as described, for example, in WO2004094429.

In one embodiment of the invention, the compound of the formula I is administered in combination with CB2 (cannabinoid receptor) agonists as described, for example, in US2005/143448.

In one embodiment of the invention, the compound of the formula I is administered in combination with histamine 1 agonists as described, for example, in WO2005101979.

In one embodiment of the invention, the compound of the formula I is administered in combination with bupropion, as described in WO2006017504.

In one embodiment of the invention, the compound of the formula I is administered in combination with opioid antagonists as described, for example, in WO2005107806 or WO2004094429.

In one embodiment of the invention, the compound of the formula I is administered in combination with neutral endopeptidase inhibitors as described, for example, in WO200202513, WO2002/06492, WO 2002040008, WO2002040022 or WO2002047670.

In one embodiment of the invention, the compound of the formula I is administered in combination with NPY inhibitors (neuropeptide Y) as described, for example, in WO2002047670.

In one embodiment of the invention, the compound of the formula I is administered in combination with sodium/hydrogen exchange inhibitors as described, for example, in WO2003092694.

In one embodiment of the invention, the compound of the formula I is administered in combination with modulators of the glucocorticoid receptor as described, for example, in WO2005090336.

In one embodiment of the invention, the compound of the formula I is administered in combination with nicotine receptor agonists as described, for example, in WO2004094429.

In one embodiment of the invention, the compound of the formula I is administered in combination with NRIs (norepinephrine reuptake inhibitors) as described, for example, in WO2002053140.

In one embodiment of the invention, the compound of the formula I is administered in combination with MOA (E-beta-methoxyacrylate), such as, for example, segeline, or as described, for example, in WO2002053140.

In one embodiment of the invention, the compound of the formula I is administered in combination with antithrombotic active ingredients, such as, for example, clopidogrel.

It is to be understood that each suitable combination of the compounds according to the invention with one or more of the compounds mentioned above and optionally one or more further pharmacologically active substances is meant to be included in the scope of the present invention.

The formulae for some of the development codes mentioned above are given below:

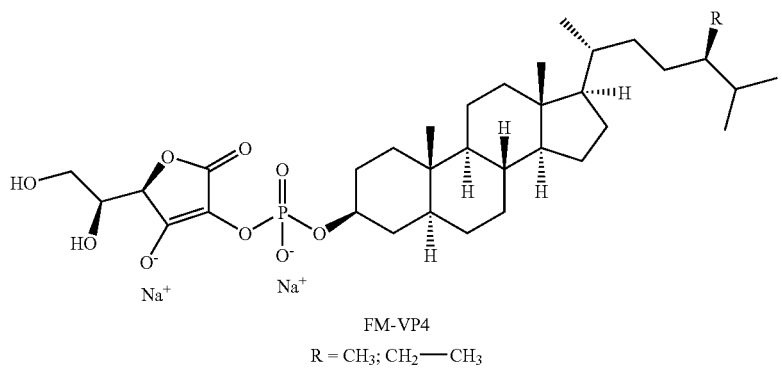

FM-VP4

R = CH$_3$; CH$_2$—CH$_3$

-continued
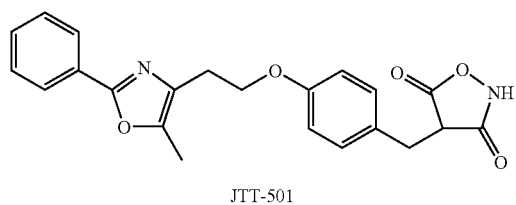
JTT-501
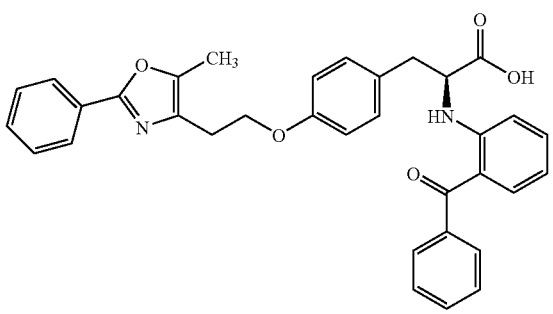
GI 262570
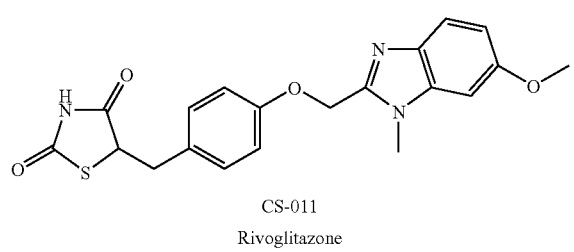
CS-011
Rivoglitazone
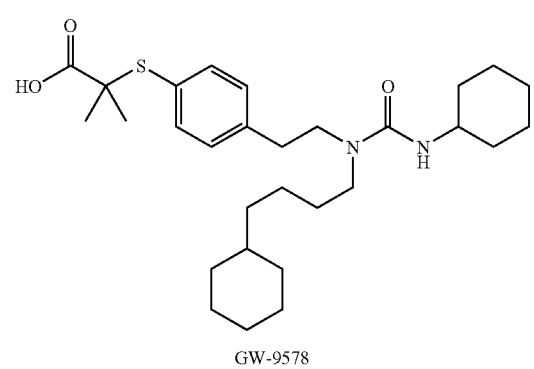
GW-9578
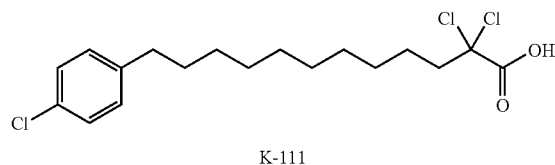
K-111
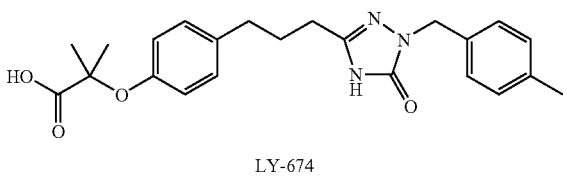
LY-674
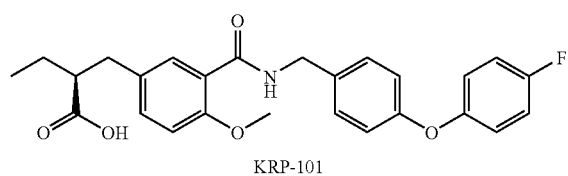
KRP-101
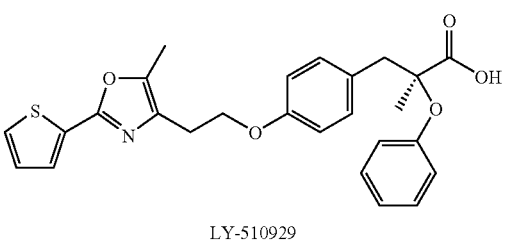
LY-510929
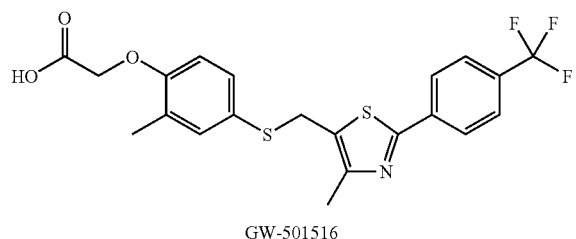
GW-501516
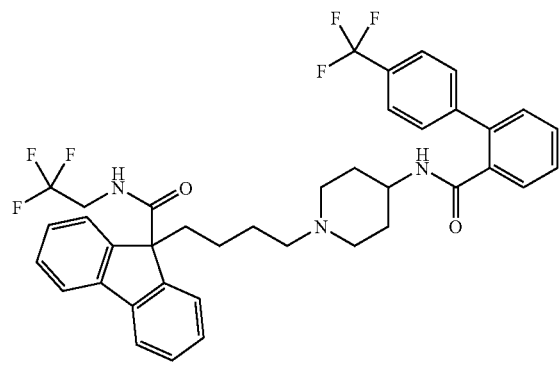
BMS-201038

-continued
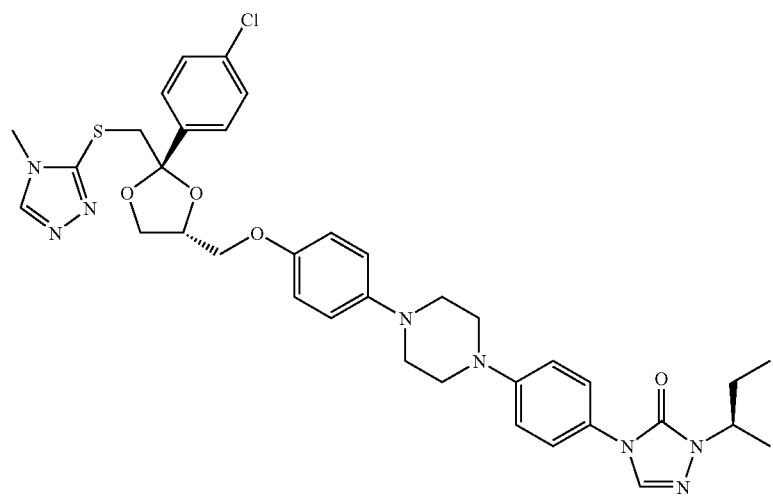
R-103757
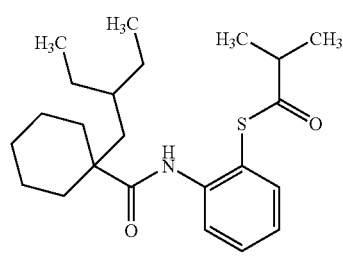
JTT-705
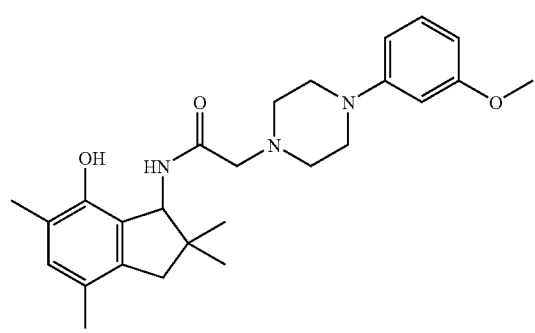
OPC-14117
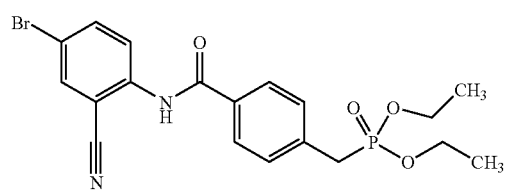
NO-1886
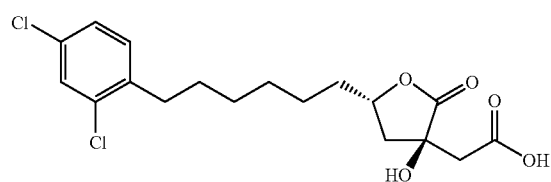
SB-204990
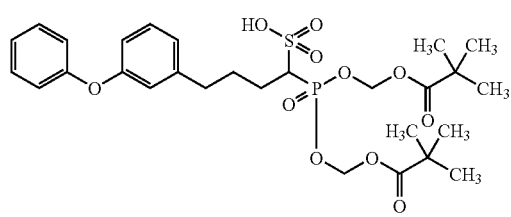
BMS-188494
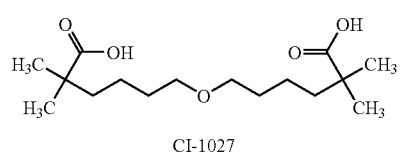
CI-1027
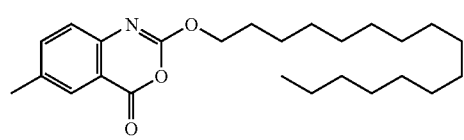
ATL-962
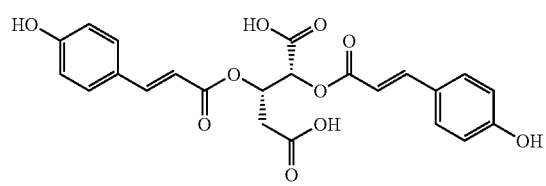
FR-258900

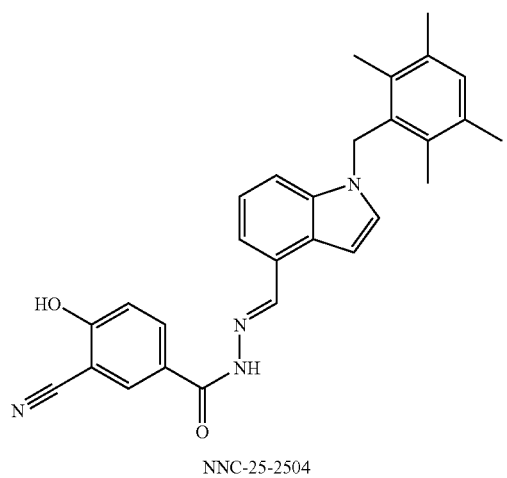
NNC-25-2504
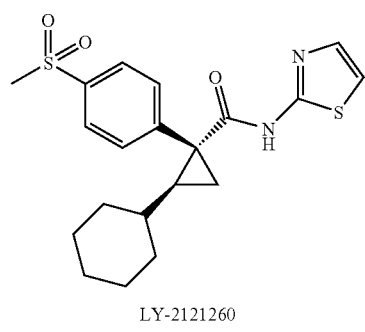
LY-2121260
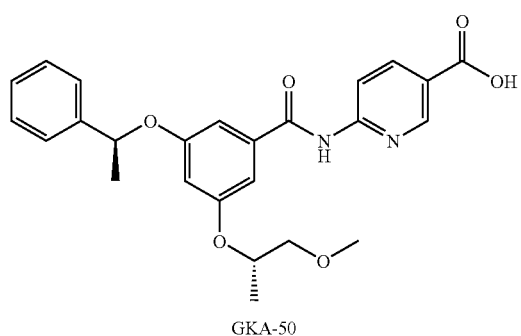
GKA-50
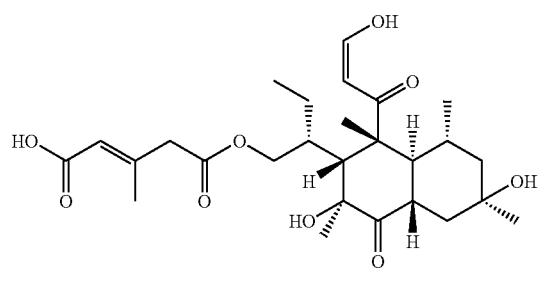
FR-225654
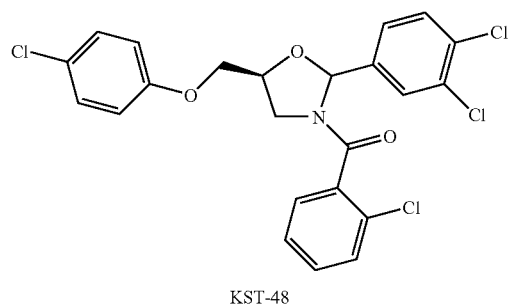
KST-48
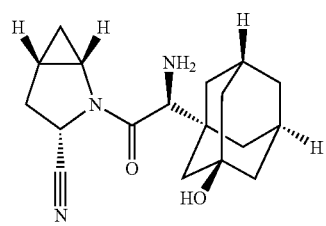
BMS-477118
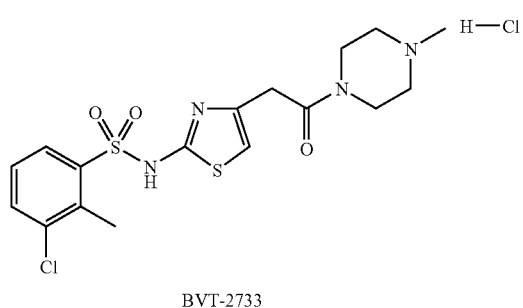
BVT-2733
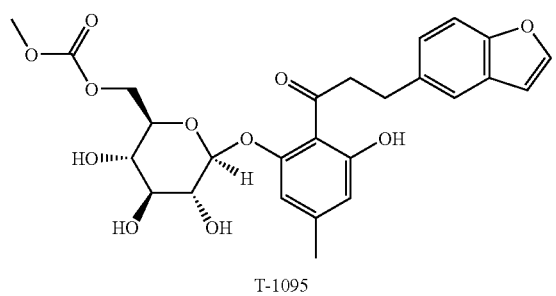
T-1095

-continued
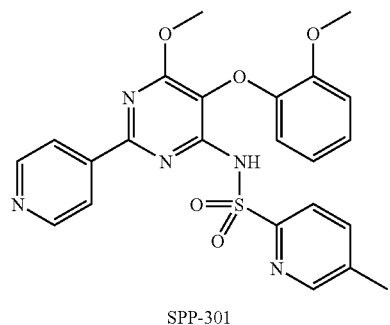
SPP-301
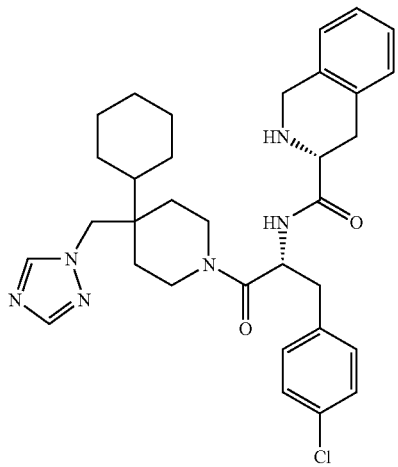
THIQ
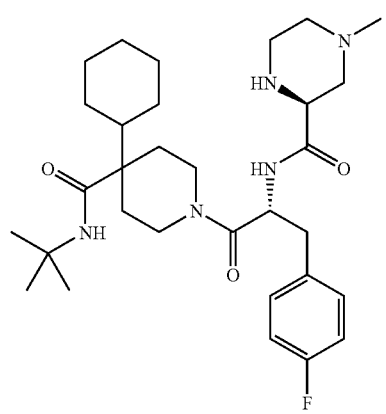
MB243
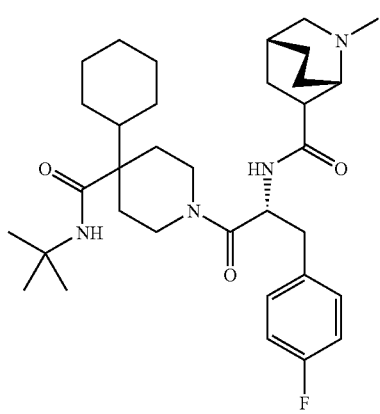
RY764
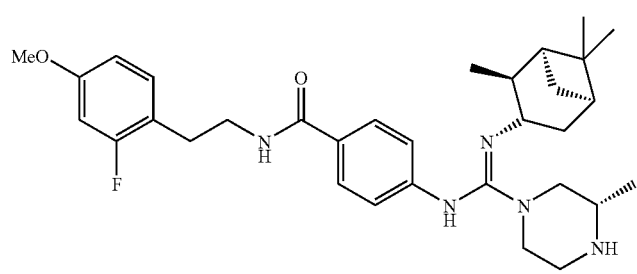
CHIR-785
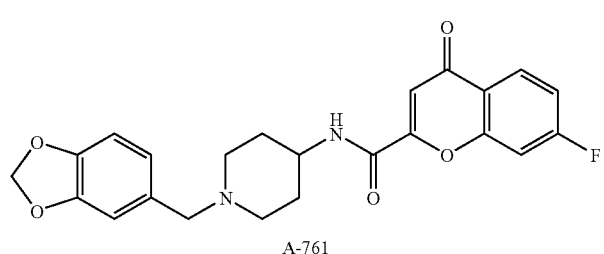
A-761

-continued
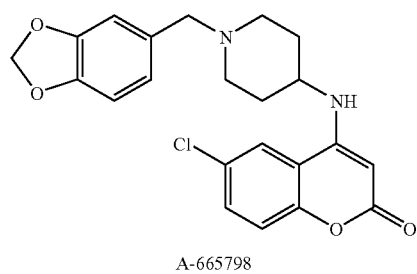
A-665798
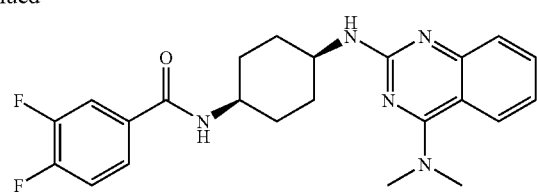
ATC-0175
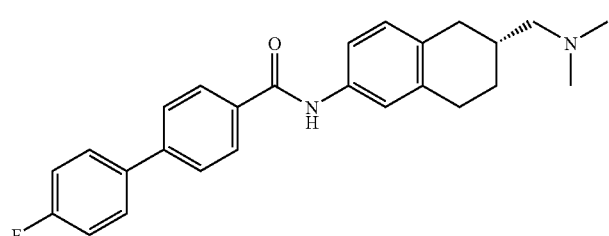
T-226296
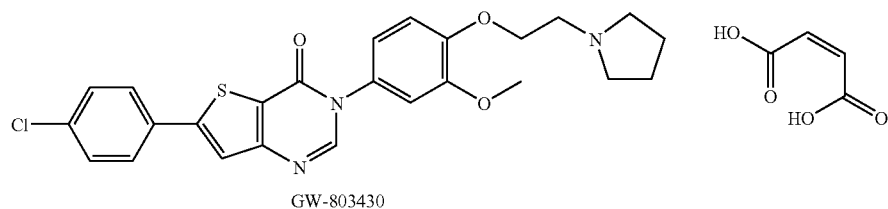
GW-803430
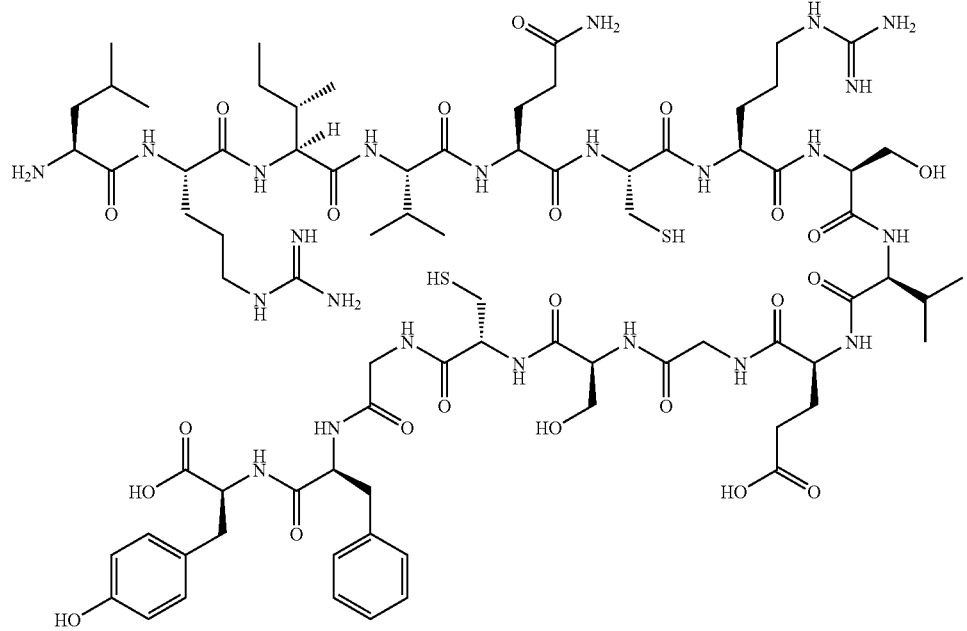
AOD-9604

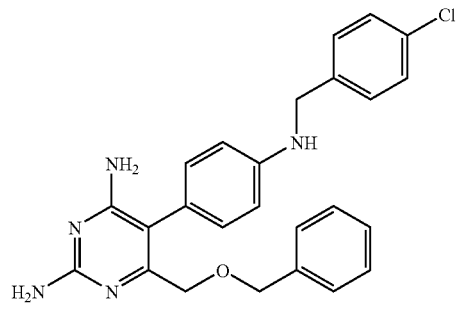

A-778193

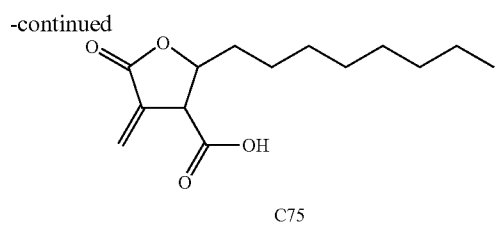

C75

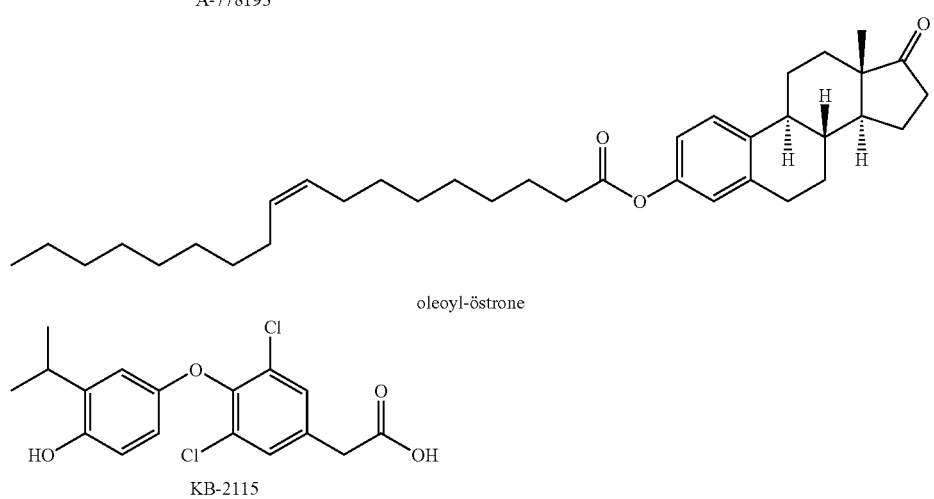

oleoyl-östrone

KB-2115

The activity of the compounds was tested as follows:

Determination of EC50 Values of PPAR Agonists in the Cellular PPARalpha Assay

Principle

The potency of substances which bind to human PPARalpha and activate it in an agonistic manner is analyzed using a stably transfected HEK cell line (HEK=human embryo kidney) which is referred to here as PPARalpha reporter cell line. It contains two genetic elements, a luciferase reporter element (pdeltaM-GAL4-Luc-Zeo) and a PPARalpha fusion protein (GR-GAL4-humanPPARalpha-LBD) which mediates expression of the luciferase reporter element depending on a PPARalpha ligand. The stably and constitutively expressed fusion protein GR-GAL4-humanPPARalpha-LBD binds in the cell nucleus of the PPARalpha reporter cell line via the GAL4 protein portion to the GAL4 DNA binding motifs 5'-upstream of the luciferase reporter element which is stably integrated in the genome of the cell line. There is only weak expression of the luciferase reporter gene in the absence of a PPARalpha ligand if fatty acid-depleted fetal calf serum (cs-FCS) is used in the assay. PPARalpha ligands bind and activate the PPARalpha fusion protein and thereby stimulate the expression of the luciferase reporter gene. The luciferase which is formed can be detected by means of chemiluminescence via an appropriate substrate.

Construction of the PPARalpha Reporter Cell Line

The PPARalpha reporter cell line was prepared in two stages. Firstly, the luciferase reporter element was constructed and stably transfected into HEK cells. For this purpose, five binding sites of the yeast transcription factor GAL4 (Accession #AF264724) were cloned in 5'-upstream of a 68 bp-long minimal MMTV promoter (Accession #V01175). The minimal MMTV promoter section contains a CCMT box and a TATA element in order to enable efficient transcription by RNA polymerase II. The cloning and sequencing of the GAL4-MMTV construct took place in analogy to the description of Sambrook J. et. al. (Molecular cloning, Cold Spring Harbor Laboratory Press, 1989). Then the complete *Photinus pyralis* gene (Accession #M15077) was cloned in 3'-downstream of the GAL4-MMTV element. After sequencing, the luciferase reporter element consisting of five GAL4 binding sites, MMTV promoter and luciferase gene was recloned into a plasmid which confers zeocin resistance in order to obtain the plasmid pdeltaM-GAL4-Luc-Zeo. This vector was transfected into HEK cells in accordance with the statements in Ausubel, F. M. et al. (Current protocols in molecular biology, Vol. 1-3, John Wiley & Sons, Inc., 1995). Then zeocin-containing medium (0.5 mg/ml) was used to select a suitable stable cell clone which showed very low basal expression of the luceriferase gene.

In a second step, the PPARalpha fusion protein (GR-GAL4-humanPPARalpha-LBD was introduced into the stable cell clone described. For this purpose, initially the cDNA coding for the N-terminal 76 amino acids of the glucocorticoid receptor (Accession #P04150) was linked to the cDNA section coding for amino acids 1-147 of the yeast transcription factor GAL4 (Accession #P04386). The cDNA of the ligand-binding domain of the human PPARalpha receptor (amino acids S167-Y468; Accession #S74349) was cloned in at the 3'-end of this GR-GAL4 construct. The fusion construct prepared in this way (GR-GAL4-humanPPARalpha-LBD) was recloned into the plasmid pcDNA3 (Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line which contains a luciferase reporter element and constitutively expresses the PPARalpha fusion protein (GR-GAL4-human PPARalpha-LBD) was isolated by selection with zeocin (0.5 mg/ml) and G418 (0.5 mg/ml).

Assay Procedure

The activity of PPARalpha agonists is determined in a 3-day assay which is described below:

Day 1

The PPARalpha reporter cell line is cultivated to 80% confluence in DMEM (#41965-039, Invitrogen) which is mixed with the following additions: 10% cs-FCS (fetal calf serum; #SH-30068.03, Hyclone), 0.5 mg/ml zeocin (#R250-01, Invitrogen), 0.5 mg/ml G418 (#10131-027, Invitrogen), 1% penicillin-streptomycin solution (#15140-122, Invitrogen) and 2 mM L-glutamine (#25030-024, Invitrogen). The cultivation takes place in standard cell culture bottles (#353112, Becton Dickinson) in a cell culture incubator at 37° C. in the presence of 5% CO2. The 80%-confluent cells are washed once with 15 ml of PBS (#14190-094, Invitrogen), treated with 3 ml of trypsin solution (#25300-054, Invitrogen) at 37° C. for 2 min, taken up in 5 ml of the DMEM described and counted in a cell counter. After dilution to 500.000 cells/ml, 35,000 cells are seeded in each well of a 96 well microtiter plate with a clear plastic base (#3610, Corning Costar). The plates are incubated in the cell culture incubator at 37° C. and 5% CO2 for 24 h.

Day 2

PPARalpha agonists to be tested are dissolved in DMSO in a concentration of 10 mM. This stock solution is diluted in DMEM (#41965-039, Invitrogen) which is mixed with 5% cs-FCS (#SH-30068.03, Hyclone), 2 mM L-glutamine (#25030-024, Invitrogen) and the previously described antibiotics (zeocin, G418, penicillin and streptomycin). Test substances are tested in 11 different concentrations in the range from 10 µM to 100 pM. More potent compounds are tested in concentration ranges from 1 µM to 10 pM or between 100 nM and 1 pM.

The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96 well microtiter plate. The DMSO concentration in the assay is less than 0.1% v/v in order to avoid cytotoxic effects of the solvent.

Each plate was charged with a standard PPARalpha agonist, which was likewise diluted in 11 different concentrations, in order to demonstrate the functioning of the assay in each individual plate. The assay plates are incubated in an incubator at 37° C. and 5% CO2 for 24 h.

Day 3

The PPARalpha reporter cells treated with the test substances are removed from the incubator, and the medium is aspirated off. The cells are lyzed by pipetting 50 µl of Bright Glo reagent (from Promega) into each well of a 96 well microtiter plate. After incubation at room temperature in the dark for 10 minutes, the microtiter plates are measured in the luminometer (Trilux from Wallac). The measuring time for each well of a microtiter plate is 1 sec.

Evaluation

The raw data from the luminometer are transferred into a Microsoft Excel file. Dose-effect plots and EC50 values of PPAR agonists are calculated using the XL.Fit program as specified by the manufacturer (IDBS).

Determination of EC50 Values of PPAR Agonists in the Cellular PPARdelta Assay

Principle

The potency of substances which bind to human PPARdelta and activate it in an agonistic manner is analyzed using a stably transfected HEK cell line (HEK=human embryo kidney) which is referred to here as PPARdelta reporter cell line. In analogy to the assay described for PPARalpha, the PPARdelta reporter cell line also contains two genetic elements, a luciferase reporter element (pdeltaM-GAL4-Luc-Zeo) and a PPARdelta fusion protein (GR-GAL4-humanPPARdelta-LBD) which mediates expression of the luciferase reporter element depending on a PPARdelta ligand. The stably and constitutively expressed fusion protein GR-GAL4-humanPPARdelta-LBD binds in the cell nucleus of the PPARdelta reporter cell line via the GAL4 protein portion to the GAL4 DNA binding motifs 5'-upstream of the luciferase reporter element which is stably integrated in the genome of the cell line. There is only little expression of the luciferase reporter gene in the absence of a PPARdelta ligand if fatty acid-depleted fetal calf serum (cs-FCS) is used in the assay. PPARdelta ligands bind and activate the PPARdelta fusion protein and thereby stimulate expression of the luciferase reporter gene. The luciferase which is formed can be detected by means of chemiluminescence via an appropriate substrate.

Construction of the PPARdelta Reporter Cell Line

The production of the stable PPARdelta reporter cell line is based on a stable HEK-cell clone which was stably transfected with a luciferase reporter element. This step was already described above in the section "construction of the PPARalpha reporter cell line". In a second step, the PPARdelta fusion protein (GR-GAL4-humanPPARdelta-LBD was stably introduced into this cell clone. For this purpose, the cDNA coding for the N-terminal 76 amino acids of the glucocorticoid receptor (Accession #P04150) was linked to the cDNA section coding for amino acids 1-147 of the yeast transcription factor GAL4 (Accession #P04386). The cDNA of the ligand-binding domain of the human PPARdelta receptor (amino acids S139-Y441; Accession #L07592) was cloned in at the 3'-end of this GR-GAL4 construct. The fusion construct prepared in this way (GR-GAL4-humanPPARdelta-LBD) was recloned into the plasmid pcDNA3 (Invitrogen) in order to enable constitutive expression by the cytomegalovirus promoter. This plasmid was linearized with a restriction endonuclease and stably transfected into the previously described cell clone containing the luciferase reporter element. The resulting PPARdelta reporter cell line which contains a luciferase reporter element and constitutively expresses the PPARdelta fusion protein (GR-GAL4-human PPARdelta-LBD) was isolated by selection with zeocin (0.5 mg/ml) and G418 (0.5 mg/ml).

Assay Procedure and Evaluation

The activity of PPARdelta agonists is determined in a 3-day assay in exact analogy to the procedure already described for the PPARalpha reporter cell line except that the PPARdelta reporter cell line and a specific PPARdelta agonist was used as a standard to control test efficacy.

PPARdelta EC50 values in the range from 1 nM to >10 µM were measured for the PPAR agonists of Examples 1 to 25 described in this application. Compounds of the invention of the formula I activate the PPARdelta receptor partially.

Determination of EC50 Values of PPAR Agonists in the Cellular PPARgamma Assay

Principle

A transient transfection system is employed to determine the cellular PPARgamma activity of PPAR agonists. It is based on the use of a luciferase reporter plasmid (pGL3basic-5xGAL4-TK) and of a PPARgamma expression plasmid (pcDNA3-GAL4-humanPPARgammaLBD). Both plasmids are transiently transfected into human embryonic kidney cells (HEK cells). There is then expression in these cells of the fusion protein GAL4-humanPPARgammaLBD which binds to the GAL4 binding sites of the reporter plasmid. In the presence of a PPARgamma-active ligand, the activated fusion protein GAL4-humanPPARgammaLBD induces expression of the luciferase reporter gene, which can be detected in the form of a chemiluminescence signal after addition of a luciferase substrate. As a difference from the stably transfected PPARalpha reporter cell line, in the cellular PPARgamma assay the two components (luciferase reporter plasmid and PPARgamma expression plasmid) are transiently transfected into HEK cells because stable and permanent expression of the PPARgamma fusion protein is cytotoxic.

Construction of the Plasmids

The luciferase reporter plasmid pGL3basic-5xGAL4-TK is based on the vector pGL3basic from Promega. The reporter plasmid is prepared by cloning five binding sites of the yeast transcription factor GAL4 (each binding site with the sequence 5'-CTCGGAGGACAGTACTCCG-3'), together with a 160 bp-long thymidine kinase promoter section (Genbank Accession #AF027128) 5'-upstream into pGL3basic. 3'-downstream of the thymidine kinase promoter is the complete luciferase gene from *Photinus pyralis* (Genbank Accession #M15077) which is already a constituent of the plasmid pGL3basic used. The cloning and sequencing of the reporter plasmid pGL3basic-5xGAL4-TK took place in analogy to the description in Sambrook J. et. al. (Molecular cloning, Cold Spring Harbor Laboratory Press, 1989).

The PPARgamma expression plasmid pcDNA3-GAL4-humanPPARgammaLBD was prepared by first cloning the cDNA coding for amino acids 1-147 of the yeast transcription factor GAL4 (Genbank Accession #P04386) into the plasmid pcDNA3 (from Invitrogen) 3'-downstream of the cytomegalovirus promoter. Subsequently, the cDNA of the ligand-binding domain (LBD) of the human PPARgamma receptor (amino acids I152-Y475; Accession #g1480099) 3'-downstream of the GAL4 DNA binding domain. Cloning and sequencing of the PPARgamma expression plasmid pcDNA3-GAL4-humanPPARgammaLBD again took place in analogy to the description in Sambrook J. et. al. (Molecular cloning, Cold Spring Harbor Laboratory Press, 1989). Besides the luciferase reporter plasmid pGL3basic-5xGAL4-TK and the PPARgamma expression plasmid pcDNA3-GAL4-humanPPARgammaLBD, also used for the cellular PPARgamma assay are the reference plasmid pRL-CMV (from Promega) and the plasmid pBluescript SK(+) from Stratagene. All four plasmids were prepared using a plasmid preparation kit from Qiagen, which ensured a plasmid quality with a minimal endotoxin content, before transfection into HEK cells.

Assay Procedure

The activity of PPARgamma agonists is determined in a 4-day assay which is described below. Before the transfection, HEK cells are cultivated in DMEM (#41965-039, Invitrogen) which is mixed with the following additions: 10% FCS (#16000-044, Invitrogen), 1% penicillin-streptomycin solution (#15140-122, Invitrogen) and 2 mM L-glutamine (#25030-024, Invitrogen).

Day 1

Firstly, solution A, a transfection mixture which contains all four plasmids previously described in addition to DMEM, is prepared. The following amounts are used to make up 3 ml of solution A for each 96 well microtiter plate for an assay: 2622 µl of antibiotic- and serum-free DMEM (#41965-039, Invitrogen), 100 µl of reference plasmid pRL-CMV (1 ng/µl), 100 µl of luciferase reporter plasmid pGL3basic-5xGAL4-TK (10 ng/µl), 100 µl of PPARgamma expression plasmid pcDNA3-GAL4-humanPPARgammaLBD (100 ng/µl) and 78 µl of plasmid pBluescript SK(+) (500 ng/µl). Then 2 ml of solution B are prepared by mixing 1.9 ml of DMEM (#41965-039, Invitrogen) with 100 µl of PolyFect transfection reagent (from Qiagen) for each 96 well microtiter plate. Subsequently, 3 ml of solution A are mixed with 2 ml of solution B to give 5 ml of solution C, which is thoroughly mixed by multiple pipetting and incubated at room temperature for 10 min.

80%-confluent HEK cells from a cell culture bottle with a capacity of 175 cm2 are washed once with 15 ml of PBS (#14190-094, Invitrogen) and treated with 3 ml of trypsin solution (#25300-054, Invitrogen) at 37° C. for 2 min. The cells are then taken up in 15 ml of DMEM (#41965-039, Invitrogen) which is mixed with 10% FCS (#16000-044, Invitrogen), 1% penicillin-streptomycin solution (#15140-122, Invitrogen) and 2 mM L-glutamine (#25030-024, Invitrogen). After the cell suspension has been counted in a cell counter, the suspension is diluted to 250,000 cells/ml. 15 ml of this cell suspension are mixed with 5 ml of solution C for one microtiter plate. 200 µl of the suspension are seeded in each well of a 96 well microtiter plate with a clear plastic base (#3610, Corning Costar). The plates are incubated in a cell culture incubator at 37° C. and 5% CO2 for 24 h.

Day 2

PPAR agonists to be tested are dissolved in DMSO in a concentration of 10 mM. This stock solution is diluted in DMEM (#41965-039, Invitrogen) which is mixed with 2% Ultroser (#12039-012, Biosepra), 1% penicillin-streptomycin solution (#15140-122, Invitrogen) and 2 mM L-glutamine (#25030-024, Invitrogen). Test substances are tested in a total of 11 different concentrations in the range from 10 µM to 100 pM. More potent compounds are tested in concentration ranges from 1 µM to 10 pM.

The medium of the HEK cells transfected and seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96 well microtiter plate. Each plate is charged with a standard PPARgamma agonist, which is likewise diluted in 11 different concentrations, in order to demonstrate the functioning of the assay in each individual plate. The assay plates are incubated in an incubator at 37° C. and 5% CO2.

Day 4

After removal of the medium by aspiration, 50 µl of Dual-Glo™ reagent (Dual-Glo™ Luciferase Assay System; Promega) are added to each well in accordance with the manufacturer's instructions in order to lyze the cells and provide the substrate for the firefly luciferase (*Photinus pyralis*) formed in the cells. After incubation at room temperature in the dark for 10 minutes, the firefly luciferase-mediated chemiluminescence is measured in a measuring instrument (measuring time/well 1 sec; Trilux from Wallac). Then 50 µl of the Dual-Glo™ Stop & Glo reagent (Dual-Glo™ Luciferase Assay System; Promega) is added to each well in order to stop the activity of the firefly luciferase and provide the substrate for the *Renilla* luciferase expressed by the reference plasmid pRL-CMV. After incubation at room temperature in the dark for a further 10 minutes, a chemiluminescence mediated by the *Renilla* luciferase is again measured for 1 sec/well in the measuring instrument.

Evaluation

The crude data from the luminometer are transferred into a Microsoft Excel file. The firefly/*Renilla* luciferase activity ratio is determined for each measurement derived from one well of the microtiter plate. The dose-effect plots and EC50 values of PPAR agonists are calculated from the ratios by the XL.Fit program as specified by the manufacturer (IDBS).

PPARgamma EC50 values in the range from 1 nM to >10 µM were measured for the PPAR agonists of Examples 1 to 25 described in this application. Compounds of the invention of the formula I activate the PPARgamma receptor partially.

The examples given in Table I, where a dotted line means the point of attachment to the amide, serve to illustrate the invention, but without limiting it.

TABLE I

[Structural formula shown with substituents R1-R8, n, z, and ring A]

| Ex | R1 | R2 | R3 | R4 | R5 | R6 | R7 | R8 | n | z | A |
|---|---|---|---|---|---|---|---|---|---|---|---|
| 1 | —CH(CH$_3$)$_2$ | H | H | H | H | 2-OCH$_2$CH$_3$ | 4-CF$_3$ | H | 1 | 1 | 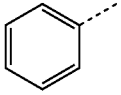 |
| 1.1 | —CH(CH$_3$)$_2$ | H | H | H | H | 2-OCH$_2$CH$_3$ | 4-CF$_3$ | H | Enan. 1 | 1 | 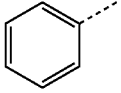 |
| 1.2 | —CH(CH$_3$)$_2$ | H | H | H | H | 2-OCH$_2$CH$_3$ | 4-CF$_3$ | H | Enan. 2 | 1 | 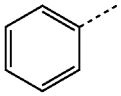 |
| 2 | —CF$_3$ | H | H | H | H | 2-OCH$_2$CH$_3$ | 4-CF$_3$ | H | 1 | 1 | 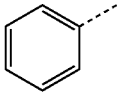 |
| 3 | —CH(CH$_3$)$_2$ | H | H | H | H | 2-(4-CF$_3$—Ph) | 4-CH$_3$ | H | 1 | 1 | 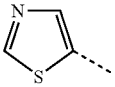 |
| 4 | Cyclopropyl | H | H | H | H | 2-(4-CF$_3$—Ph) | 4-CH$_3$ | H | 1 | 1 | 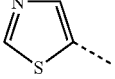 |
| 5 | —CH(CH$_3$)$_2$ | H | H | H | H | 2-OCH$_2$CH$_3$ | 4-CF$_3$ | H | 2 (S) | 1 | 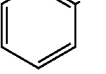 |
| 6 | —CH(CH$_3$)$_2$ | H | H | H | H | 2-OCH$_2$CH$_3$ | 4-CF$_3$ | H | 2 (R) | 1 | 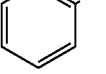 |
| 7 | —CH(CH$_3$)$_2$ | 5-Cl | H | H | H | 2-OCH$_2$CH$_3$ | 4-CF$_3$ | H | 1 | 1 | 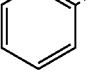 |

TABLE I-continued

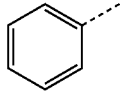

| Ex | R1 | R2 | R3 | R4 | R5 | R6 | R7 | R8 | n | z | A |
|---|---|---|---|---|---|---|---|---|---|---|---|
| 8 | —CH(CH$_3$)$_2$ | 6-OCH$_3$ | H | H | H | 2-OCH$_2$CH$_3$ | 4-CF$_3$ | H | 1 | 1 | 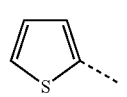 |
| 9 | —CH(CH$_3$)$_2$ | 5-Cl | H | H | H | 3-OCH$_2$CH$_3$ | 5-CF$_3$ | H | 1 | 1 | 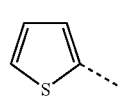 |
| 10 | —CH(CH$_3$)$_2$ | 6-OCH$_3$ | H | H | H | 3-OCH$_2$CH$_3$ | 5-CF$_3$ | H | 1 | 1 | 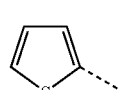 |
| 11 | —CH(CH$_3$)$_2$ | H | H | H | H | 3-OCH$_2$CH$_3$ | 5-CF$_3$ | H | 1 | 1 | 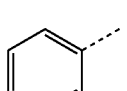 |
| 12 | —CH(CH$_3$)$_2$ | H | H | H | H | 2-OCH$_2$CH$_3$ | 4-CF$_3$ | H | 2 | 2 | 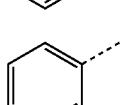 |
| 13 | —CH(CH$_3$)$_2$ | H | H | H | H | 2-Cl | 5-CF$_3$ | H | 1 | 1 | 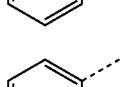 |
| 14 | —CH(CH$_3$)$_2$ | H | H | H | H | 2-CH$_3$ | 4-Cl | H | 1 | 1 | 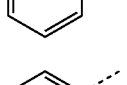 |
| 15 | —CH(CH$_3$)$_2$ | H | H | H | H | 2-F | 4-CF$_3$ | 3-F | 1 | 1 | 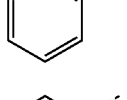 |
| 16 | —CH(CH$_3$)$_2$ | H | H | H | H | 2-F | 4-CF$_3$ | H | 1 | 1 | 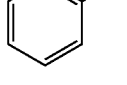 |
| 17 | —CH(CH$_3$)$_2$ | H | H | H | H | 2-OCH$_3$ | 4-Cl | H | 1 | 1 | 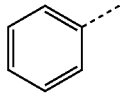 |
| 18 | —CH(CH$_3$)$_2$ | H | H | H | H | 2-Cl | 4-Cl | H | 1 | 1 | 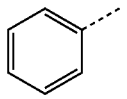 |
| 19 | —CH(CH$_3$)$_2$ | 5-F | H | H | H | 2-OCH$_2$CH$_3$ | 4-CF$_3$ | H | 1 | 1 | |

TABLE I-continued

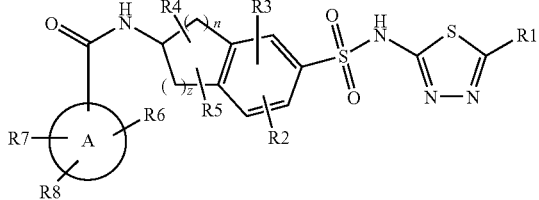

| Ex | R1 | R2 | R3 | R4 | R5 | R6 | R7 | R8 | n | z | A |
|----|----|----|----|----|----|----|----|----|---|---|---|
| 20 | —CH(CH$_3$)$_2$ | H | H | H | 1-CH$_3$ | 2-OCH$_2$CH$_3$ | 4-CF$_3$ | H | 1 | 1 | 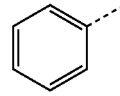 |
| 21 | —CH(CH$_3$)$_2$ | 6-O—CH$_2$CF$_3$ | H | H | H | 2-OCH$_2$CH$_3$ | 4-CF$_3$ | H | 1 | 1 | 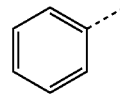 |
| 22 | Cyclopropyl | H | H | H | H | 2-OCH$_2$CH$_3$ | 4-CF$_3$ | H | 1 | 1 | 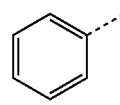 |
| 23 | Phenyl | H | H | H | H | 2-OCH$_2$CH$_3$ | 4-CF$_3$ | H | 1 | 1 | 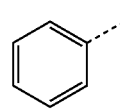 |
| 24 | Cyclohexyl | H | H | H | H | 2-OCH$_2$CH$_3$ | 4-CF$_3$ | H | 1 | 1 | 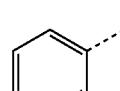 |
| 25 | —CH(CH$_3$)$_2$ | H | H | H | H | 3-OCH$_3$ | H | H | 1 | 1 | 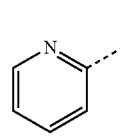 |

The potency of some of the described examples are indicated in the following table:

| Example | PPARdelta EC50 (μM) | PPARgamma EC50 (μM) |
|---------|---------------------|---------------------|
| 1 | 0.001 | 0.001 |
| 1.1 | 0.001 | 0.022 |
| 1.2 | 0.05 | >10 |
| 5 | 0.6 | 0.1 |
| 6 | 0.6 | 0.2 |
| 11 | 0.001 | >10 |

Processes

The compounds of the general formula I according to the invention where A, n, z, R1, R2, R3, R4, R5, R6, R7, R8 are as defined can be obtained as outlined in the reaction schemes below:

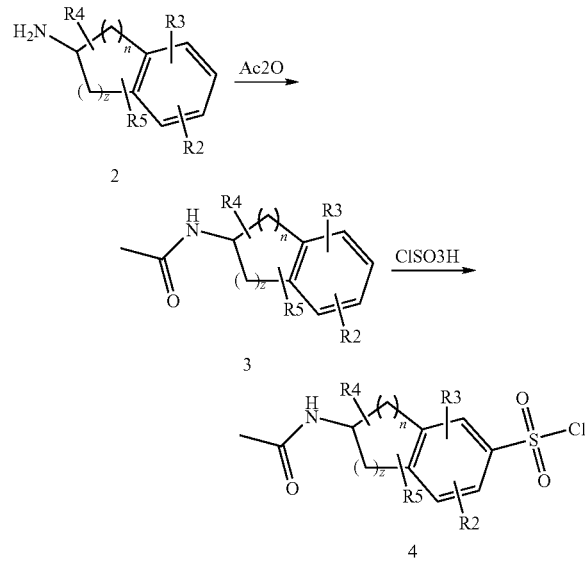

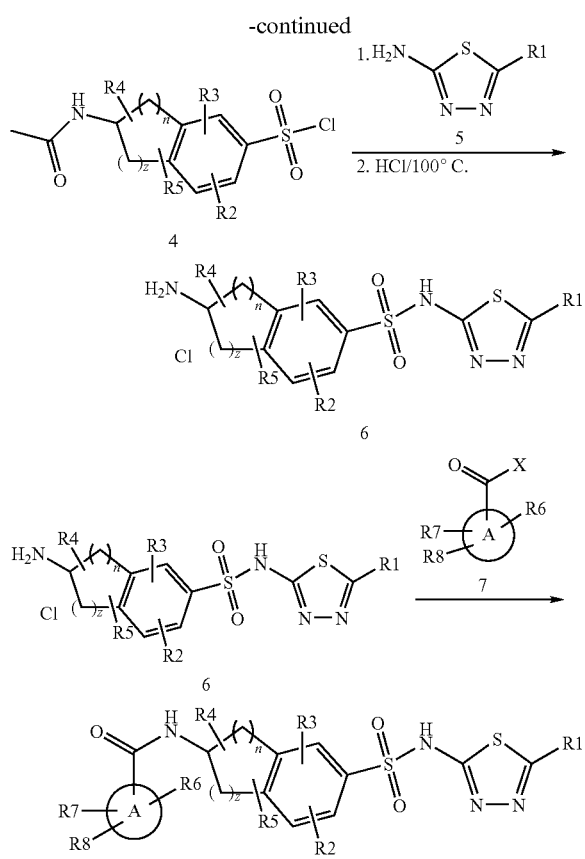

An amino bicyclic compound of general formula 2 is treated with an acylating agent like acetic anhydride or acetyl chloride to yield the intermediate 3, which on action with chlorosulfonic acid leads the benzenesulfonyl chloride of general formula 4. The benzenesulfonyl chloride of general formula 4 is coupled with the [1,3,4]thiadiazol-2-ylamine of the general formula 5 in the presence of a base or in a basic solvent like pyridine to obtain the sulfonyl amide that after refluxing in 2N hydrochloric acid to remove the N-acetyl group gives the amine of general formula 6 as its hydrochloric acid salt.

The amine of general formula 6 is coupled with a carboxylic acid of general formula 7, where X=OH, with a coupling reagent as O-((Ethoxycarbonyl)cyanomethyleneamino)-N,N,N',N'-tetramethyluronium tetrafluoroborate in the presence of a base such as triethylamine in an appropriate solvent like dimethylformamide or tetrahydrofuran to obtain the compound of general formula 1. Alternatively the amine of general formula 6 is coupled with a carbonyl chloride of general formula 7, where X=Cl— or with other known derivatives of acids that are able to react with amines—in a solvent as dichloromethane and in the presence of a base like triethylamine to obtain the compound of general formula 1.

A further method to prepare the compounds of the general formula 1 consists in the acylation of the amino indanes 2 with the carboxylic acid derivatives 7 and the subsequent reaction with chloro sulfonic acid followed by reaction with the amino heterocycle 5.

List of Abbreviation:

| | |
|---|---|
| Ac | acetyl |
| AIBN | 2,2'-azobis(2-methylpropionitrile) |
| Bn | benzyl |
| BOC | tert-butyl-oxy-carbonyl |
| iBu | isobutyl |
| tBu | tert-butyl |
| BuLi | n-butyllithium |
| Bz | benzoyl |
| Cy | cyclohexyl |
| DBU | 1,8-diazabicyclo[5.4.0]undec-7-ene |
| DCI | direct chemical ionization (MS) |
| DCM | dichloromethane |
| DMAP | N,N-dimethylaminopyridine |
| DMF | N,N-dimethylformamide |
| DMSO | dimethylsulfoxide |
| EE | ethyl acetate |
| eq | equivalents |
| ESI | electrospray-Ionisation (MS) |
| FG | leaving group |
| GC | gas chromatography |
| Hal | halogen |
| HPLC | high performance liquid chromatography |
| LC-MS | liquid chromatography coupled with mass-spectroscopy |
| Me | methyl |
| MeCN | acetonitrile |
| MS | mass-spectroscopy |
| MS 4A | molecular sieves four angström |
| MsCl | methanesulfonylchloride |
| MW | micro wave |
| NBS | N-bromosuccinimide |
| NMR | nuclear magnetic resonance |
| p | para |
| Pd/C | palladium on carbon |
| iPr | isopropyl |
| nPr | n-propyl |
| Rf | retention factor (TLC) |
| tert | tertiary |
| TFA | trifluoroacetic acid |
| THF | tetrahydrofuran |
| TLC | thin layer chromatography |
| TOTU | O-((ethoxycarbonyl)cyanomethyleneamino)-N,N,N',N'-tetramethyluronium-tetrafluoroborate |

EXPERIMENTAL PART 1) 2-Ethoxy-N-[5-(5-isopropyl-[1,3,4]thiadiazol-2-ylsulfamoyl)-indan-2-yl]-4-trifluoromethyl-benzamide

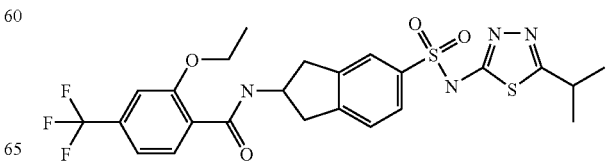

1a) 2-Methoxy-4-trifluoromethoxy-benzoic acid methyl ester

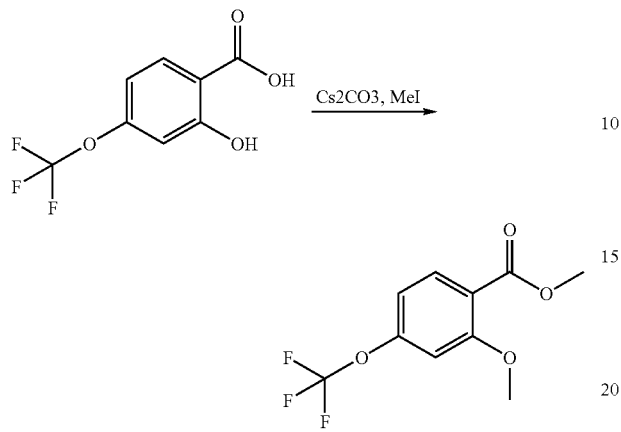

1.0 g 2-hydroxy-(trifluoromethoxy)benzoic acid were dissolved in 30 ml dimethylformamide. 640 mg iodomethane and 4.70 g cesium carbonate were added and the reaction mixture was stirred at room temperature for three hours. The reaction mixture was diluted by addition of 100 ml ethyl acetate, washed with 30 ml water and brine and then dried over MgSO4. The solvent was removed in vacuo to obtain 590 mg 2-methoxy-4-trifluoromethoxy-benzoic acid methyl ester.

MS (ESI): (M+1)=251

1b) 2-Methoxy-4-trifluoromethoxy-benzoic acid

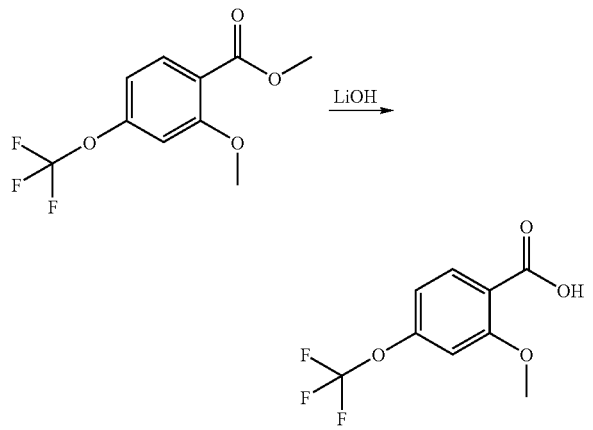

590 mg 2-Methoxy-4-trifluoromethoxy-benzoic acid methyl ester was dissolved in a mixture of 30 ml tetrahydrofuran and 10 ml water. 367 mg lithium hydroxide were added and the reaction mixture stirred at 60° C. for two hours. The cooled reaction mixture was acidified by dropwise addition of concentrated hydrochloric acid, then the mixture was extracted three times with portions of 80 ml ethyl acetate. The combined organic layers were dried over MgSO4. The solvent was removed in vacuo to obtain 518 mg 2-methoxy-4-trifluoromethoxy-benzoic acid.

MS (ESI): (M+1)=237

1c) N-Indan-2-yl-acetamide

Acetic anhydride (3.55 ml) was dropped to the mixture of 6.37 g 2-amino indane hydrochloride, 60 ml of ethyl acetate and 10.4 ml triethylamine and the reaction mixture was stirred at room temperature for 15 hours. The solvents were evaporated in vacuo and the solid residue was digested with water, filtered and dried at 40° C. in vacuo.

Yield: 5.5 g Mp.: 126.5° C.

1d) 2-Acetylamino-indan-5-sulfonyl chloride

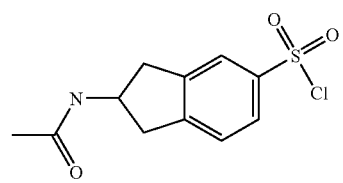

1.6 ml of chloro sulfonic acid was dropped to the stirred solution of 1.06 g N-Indan-2-yl-acetamide and 50 ml of dichloromethane and the mixture was stirred for 15 hours at room temperature. The reaction was than quenched with cold water and die organic phase separated, dried over sodium sulfate evaporated. The resulting residue was used for further reaction without further purification.

Yield: 1.4 g

1e) N-[5-(5-Isopropyl-[1,3,4]thiadiazol-2-ylsulfamoyl)-indan-2-yl]-acetamide

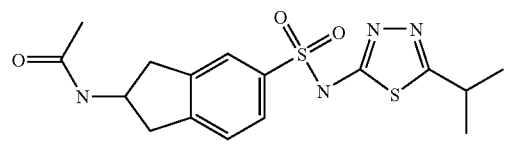

2-Acetylamino-indan-5-sulfonyl chloride (500 mg) was dissolved in 5 ml of pyridine and a catalytic amount of 4-dimethylamino pyridine was added. After addition of 262 mg of 5-isopropyl-[1,3,4]thiadiazol-2-ylamine the mixture was stirred at 60° C. for 1 hour followed by evaporation. The resulting crude material was purified by column chromatography (silica gel, eluent: dichloromethane:methanol=95:5).

Yield: 250 mg MS (ESI): (M+1)=381

1f) N-(5-Sulfamoyl-indan-2-yl)-acetamide

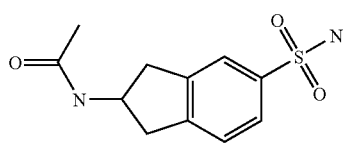

was prepared from 2-Acetylamino-indan-5-sulfonyl chloride and an excess of ammonia.

MS (ESI): (M+1)=255

1g) 2-Amino-indan-5-sulfonic acid (5-isopropyl-[1,3,4]thiadiazol-2-yl)-amide hydrochloride

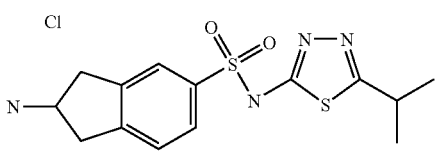

N-[5-(5-Isopropyl-[1,3,4]thiadiazol-2-ylsulfamoyl)-indan-2-yl]-acetamide (96 mg) was heated and stirred for 27 hours in 10 ml 2N hydrochloric acid at 100° C. After completion a clear solution occurred. This was evaporated to dryness and the solid residue was used without further purification.
MS (ESI): (M+1)=339

1) 2-Ethoxy-N-[5-(5-isopropyl-[1,3,4]thiadiazol-2-ylsulfamoyl)-indan-2-yl]-4-trifluoromethyl-benzamide (A003541307)

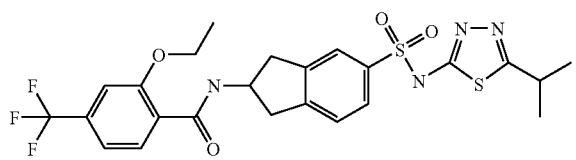

The mixture of 2-amino-indan-5-sulfonic acid (5-isopropyl-[1,3,4]thiadiazol-2-yl)-amide hydrochloride (40 mg), 1.5 ml of dimethyl formamide, 0.037 ml of triethylamine, 41 mg of HATU and 25 mg of 2-ethoxi-4-trifluoromethyl-benzoic acid was stirred at room temperature over night. The solvents were evaporated in vacuo and the resulting crude material was purified by column chromatography (silica gel, eluent: dichloromethane:methanol=95:5).
MS (ESI): (M+1)=555

1.1) 2-Ethoxy-N-[5-(5-isopropyl-[1,3,4]thiadiazol-2-ylsulfamoyl)-indan-2-yl]-4-trifluoromethyl-benzamide (Enantiomer 1)

and 1.2) 2-Ethoxy-N-[5-(5-isopropyl-[1,3,4]thiadiazol-2-ylsulfamoyl)-indan-2-yl]-4-trifluoromethyl-benzamide (Enantiomer 2)

were prepared by separation of the racemic compound of example 1 on a chiral column (chiralcel OJ-H/73, eluent: MeOH+0.1% TFA, 30° C.)

2) 2-Ethoxy-4-trifluoromethyl-N-[5-(5-trifluoromethyl-[1,3,4]thiadiazol-2-ylsulfamoyl)-indan-2-yl]-benzamide

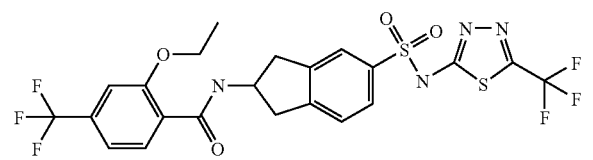

was prepared by a method similar to example 1) starting with the intermediate of example 2a).
MS (ESI): (M+1)=581

2a) N-[5-(5-Trifluoromethyl-[1,3,4]thiadiazol-2-ylsulfamoyl)-indan-2-yl]-acetamide

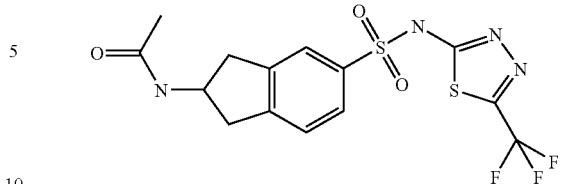

The mixture of 300 mg of 2-chloro-5-trifluoromethyl-[1,3,4]thiadiazol, 300 mg of N-(5-sulfamoyl-indan-2-yl)-acetamide, 1.8 g cesium carbonate und 10 ml of NMP was stirred at 70° C. for 3 hours. After cooling to room temperature 50 ml of water were added and with 2N hydrochloric acid a pH=3 was adjusted. The product was extracted twice with 30 ml of ethyl acetate, the organic layer was washed with 20 ml of water, dried over sodium sulfate and evaporated in vacuo. The resulting crude material was purified by column chromatography (silica gel, eluent: dichloromethane:methanol=90:10).
MS (ESI): (M+1)=407
The following compounds were prepared by similar methods:

3) 4-Methyl-2-(4-trifluormethyl-phenyl)-thiazol-5-carbonsäure-[5-(5-isopropyl-[1,3,4]thiadiazol-2-ylsulfamoyl)-indan-2-yl]-amid

MS (ESI): (M+1)=608

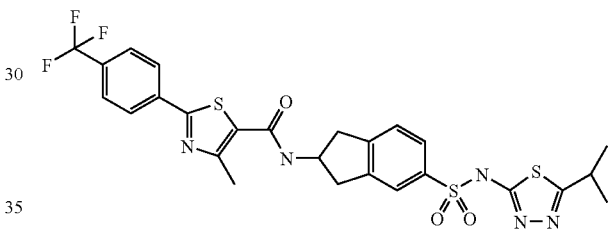

4) 4-Methyl-2-(4-trifluormethyl-phenyl)-thiazol-5-carbonsäure-[5-(5-cyclopropyl-[1,3,4]thiadiazol-2-ylsulfamoyl)-indan-2-yl]-amid

MS (ESI): (M+1)=606

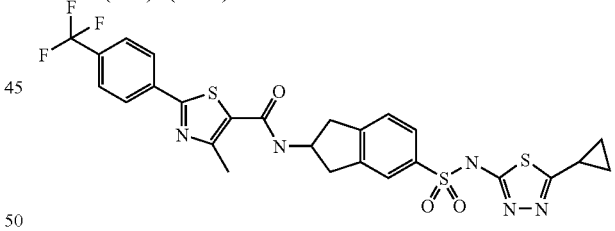

5) 2-Ethoxy-N-[(S)-7-(5-isopropyl-[1,3,4]thiadiazol-2-ylsulfamoyl)-1,2,3,4-tetrahydro-naphthalen-2-yl]-4-trifluoromethyl-benzamide

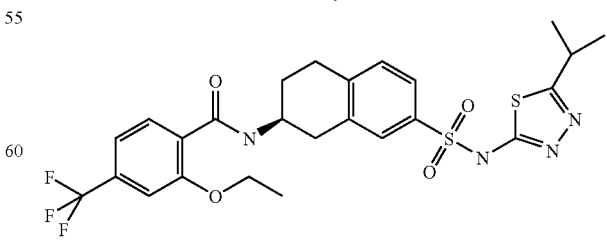

was prepared by a method similar to example 1) starting with the intermediate of example 5d).
MS (ESI): (M+1)=569

5a) (S)-N-(1,2,3,4-Tetrahydro-naphthalen-2-yl)-acetamide

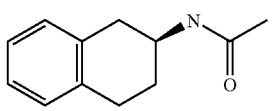

was prepared by reaction of the commercially available (S)-7-amino-5,6,7,8-tetrahydro-naphthalene with acetic anhydride according to known methods.

MS (ESI): (M+1)=190

5b) (S)-7-Acetylamino-5,6,7,8-tetrahydro-naphthalene-2-sulfonyl chloride

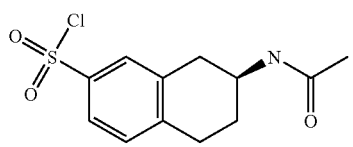

was prepared by sulfochlorination of the compound of the example 5a) with chloro sulfonic acid.

MS (ESI): (M+1)=288

5c) (S)-N-[(S)-7-(5-isopropyl-[1,3,4]thiadiazol-2-ylsulfamoyl)-1,2,3,4-tetrahydro-naphthalene-2-yl]-acetamide

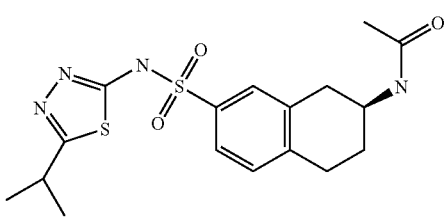

was prepared by reaction of the compound of the example 5b) with 5-isopropyl-(1,3,4)-thiadiazol-ylamine in pyridine.

MS (ESI): (M+1)=395

5d) (S)-7-Amino-5,6,7,8-tetrahydro-naphthalene-2-sulfonic acid-(5-isopropyl-[1,3,4]thiadiazol-2-yl)-amide-hydrochloride

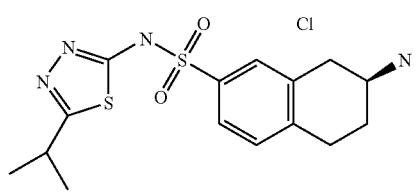

was prepared by reaction of the compound of the example 5c) with 5N hydrochloric acid at 100° C. for 25 hours.

MS (ESI): (M+1)=353

6) 2-Ethoxi-N-[(R)-7-(5-isopropyl-[1,3,4]thiadiazol-2-ylsulfamoyl)-1,2,3,4-tetrahydro-naphthalene-2-yl]-4-trifluoromethyl-benzamide

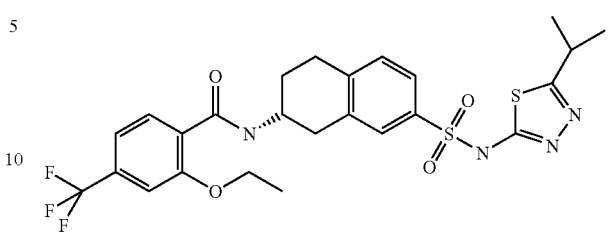

was prepared by a reaction sequence similar to the preparation of the compound of example 5) starting with the commercially available (R)-7-amino-5,6,7,8-tetrahydro-naphthalene.

MS (ESI): (M+1)=569

7) N-[5-Chloro-6-(5-isopropyl-[1,3,4]thiadiazol-2-ylsulfamoyl)-indan-2-yl]-2-ethoxy-4-trifluoromethyl-benzamide

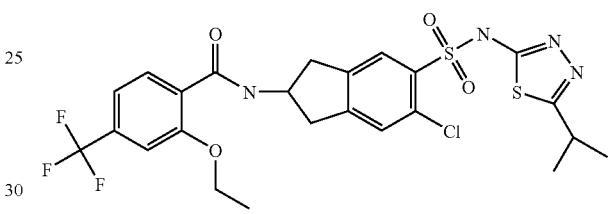

was prepared by a reaction sequence similar to the preparation of the compound of example 1) starting with 5-chloro-indan-2-ylamine.

MS (ESI): (M+1)=589

8) 2-Ethoxy-N-[5-(5-isopropyl-[1,3,4]thiadiazol-2-ylsulfamoyl)-6-methoxy-indan-2-yl]-4-trifluoromethyl-benza

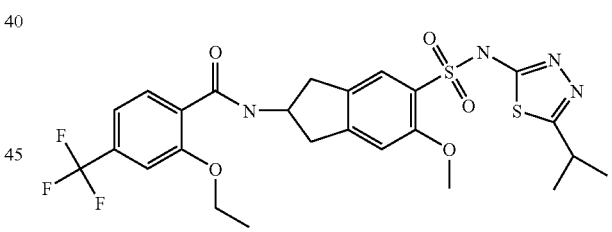

was prepared by a reaction sequence similar to the preparation of the compound of example 1) starting with 5-methoxy-indan-2-ylamine.

MS (ESI): (M+1)=585

9) 3-Ethoxy-5-trifluoromethyl-thiophene-2-carboxylic acid [5-chloro-6-(5-isopropyl-[1,3,4]thiadiazol-2-ylsulfamoyl)-indan-2-yl]-amide

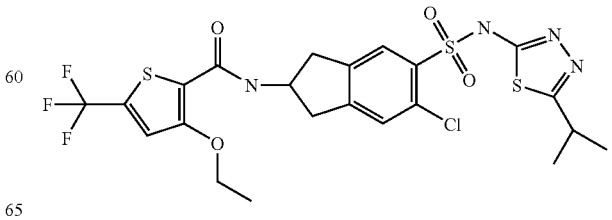

This compound was prepared by reaction of 2-Amino-6-chloro-indan-5-sulfonic acid (5-isopropyl-[1,3,4]thiadiazol- 2-yl)-hydrochloride with 3-ethoxy-5-trifluoromethyl-thiophene-2-carboxylic acid (mp.: 143.7° C.) obtained from 3-ethoxy-5-trifluoromethyl-thiophene-2-carboxylic acid methyl ester by hydrolysis with lithium hydroxide in water/methanol.

The 3-ethoxy-5-trifluoromethyl-thiophene-2-carboxylic acid methyl ester (mp.: 93.6° C.) was prepared from the known 3-hydroxy-5-trifluoromethyl-thiophene-2-carboxylic acid methyl ester (Synthesis 2000, No. 8, 1078-1080) by alkylation with ethyl iodide in the presence of cesium carbonate in DMF as solvent.

MS (ESI): MS (ESI): (M+1)=595

10) 3-Ethoxy-5-trifluoromethyl-thiophene-2-carboxylic acid [5-(5-isopropyl-[1,3,4]thiadiazol-2-ylsulfamoyl)-6-methoxy-indan-2-yl]-amide

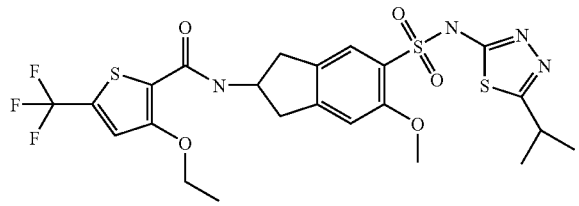

This compound was prepared similarly by reaction of 2-Amino-6-methoxi-indan-5-sulfonic acid (5-isopropyl-[1,3,4]thiadiazol-2-yl)-hydrochloride with 3-ethoxy-5-trifluoromethyl-thiophene-2-carboxylic acid.

MS (ESI): (M+1)=591

11) 3-Ethoxy-5-trifluoromethyl-thiophene-2-carboxylic acid [5-(5-isopropyl-[1,3,4]thiadiazol-2-ylsulfamoyl)-indan-2-yl]-amide

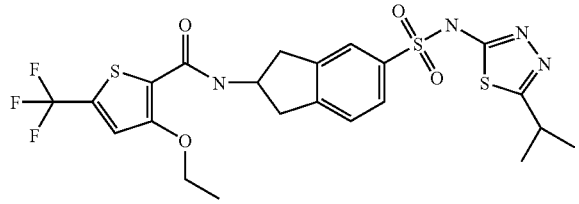

This compound was prepared similarly by reaction of 2-Amino-indan-5-sulfonic acid (5-isopropyl-[1,3,4]thiadiazol-2-yl)-hydrochloride with 3-ethoxy-5-trifluoromethyl-thiophene-2-carboxylic acid.

MS (ESI): (M+1)=561

12) 2-Ethoxy-N-[2-(5-isopropyl-[1,3,4]thiadiazol-2-ylsulfamoyl)-6,7,8,9-tetrahydro-5H-benzocyclohepten-7-yl]-4-trifluoromethyl-benzamide

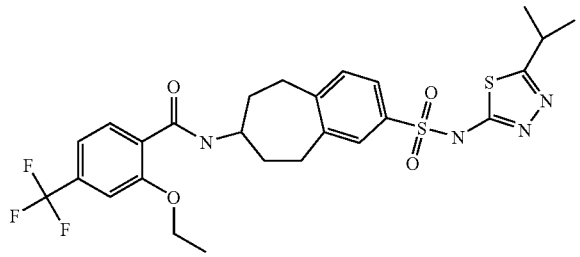

was prepared by a reaction sequence similar to the preparation of the compound of example 1) starting with 6,7,8,9-tetrahydro-5H-enzocyclohepten-7-ylamine.

MS (ESI): (M+1)=583

13) 2-Chloro-N-[5-(5-isopropyl-[1,3,4]thiadiazol-2-ylsulfamoyl)-indan-2-yl]-5-trifluoromethyl-benzamide

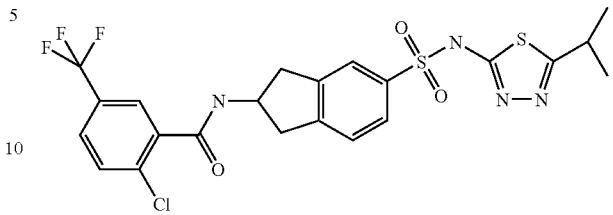

This compound was prepared similarly by reaction of 2-amino-indan-5-sulfonic acid (5-isopropyl-[1,3,4]thiadiazol-2-yl)-hydrochloride with 2-chloro-5-trifluoromethyl-benzoic acid.

MS (ESI): (M+1)=545

14) 4-Chloro-N-[5-(5-isopropyl-[1,3,4]thiadiazol-2-ylsulfamoyl)-indan-2-yl]-2-methyl-benzamide

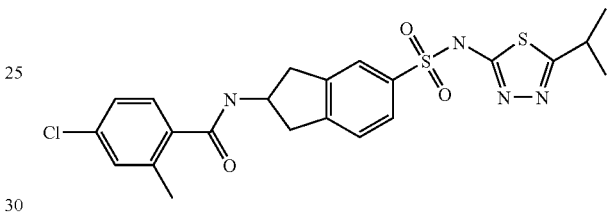

This compound was prepared similarly by reaction of 2-amino-indan-5-sulfonic acid (5-isopropyl-[1,3,4]thiadiazol-2-yl)-hydrochloride with 4-chloro-2-methyl-benzoic acid.

MS (ESI): (M+1)=491

15) 2,3-Difluoro-N-[5-(5-isopropyl-[1,3,4]thiadiazol-2-ylsulfamoyl)-indan-2-yl]-4-trifluoromethyl-benzamide

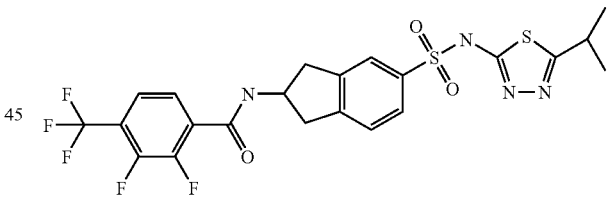

This compound was prepared similarly by reaction of 2-amino-indan-5-sulfonic acid (5-isopropyl-[1,3,4]thiadiazol-2-yl)-hydrochloride with 2,3-difluoro 4-trifluoromethyl-benzoic acid.

MS (ESI): (M+1)=547

16) 2-Fluoro-N-[5-(5-isopropyl-[1,3,4]thiadiazol-2-ylsulfamoyl)-indan-2-yl]-4-trifluoromethyl-benzamide

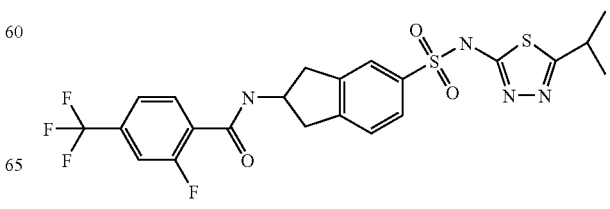

This compound was prepared similarly by reaction of 2-amino-indan-5-sulfonic acid (5-isopropyl-[1,3,4]thiadiazol-2-yl)-hydrochloride with 2-fluoro 4-trifluoromethyl-benzoic acid.
MS (ESI): (M+1)=529

17) 4-Chloro-N-[5-(5-isopropyl-[1,3,4]thiadiazol-2-ylsulfamoyl)-indan-2-yl]-2-methoxi-benzamide

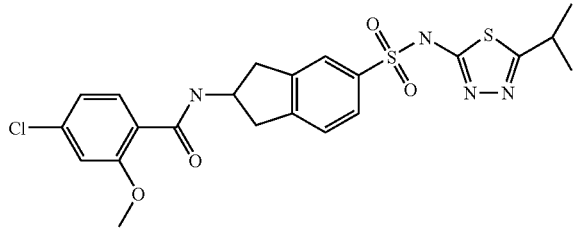

This compound was prepared similarly by reaction of 2-amino-indan-5-sulfonic acid (5-isopropyl-[1,3,4]thiadiazol-2-yl)-hydrochloride with 4-chloro-2-methoxy-benzoic acid.
MS (ESI): (M+1)=507

18) 2,4-Dichloro-N-[5-(5-isopropyl-[1,3,4]thiadiazol-2-ylsulfamoyl)-indan-2-yl]-benzamide

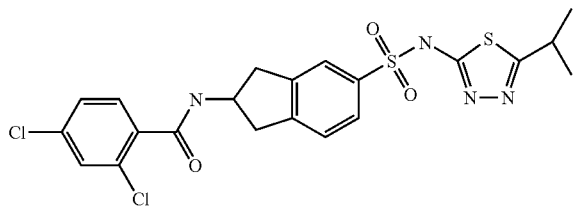

This compound was prepared similarly by reaction of 2-amino-indan-5-sulfonic acid (5-isopropyl-[1,3,4]thiadiazol-2-yl)-hydrochloride with 2,4-dichloro-benzoic acid.
MS (ESI): (M+1)=511

19) 2-Ethoxy-N-[5-fluoro-6-(5-isopropyl-[1,3,4]thiadiazol-2-ylsulfamoyl)-indan-2-yl]-4-trifluoromethyl-benzamide

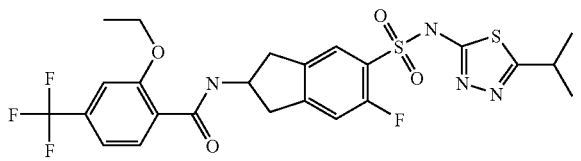

This compound was prepared similarly to the procedure described in example 1 starting from 5-fluoro-indan-2-yl-amine.
MS (ESI): (M+1)=573

20) 2-Ethoxy-N-[5-(5-isopropyl-[1,3,4]thiadiazol-2-ylsulfamoyl)-1-methyl-indan-2-yl]-4-trifluoromethyl-benzamide

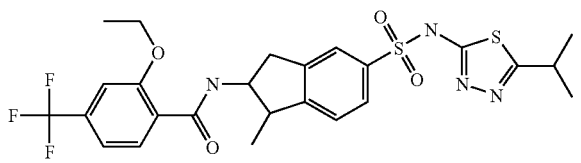

This compound was prepared similarly to the procedure described in example 1 starting from 1-methyl-indan-2-yl-amine.
MS (ESI): (M+1)=569

21) 2-Ethoxy-N-[5-(5-isopropyl-[1,3,4]thiadiazol-2-ylsulfamoyl)-6-(2,2,2-trifluoro-ethoxy)-indan-2-yl]-4-trifluoromethyl-benzamide

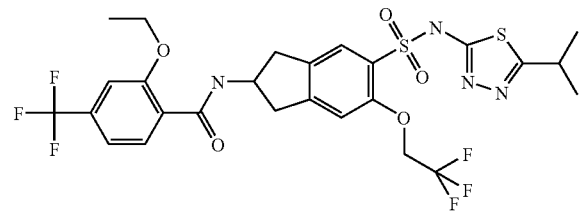

This compound was prepared similarly to the procedure described in example 1 starting from 5-(2,2,2-trifluoro-ethoxy)-indan-2-yl-amine.
MS (ESI): (M+1)=653

22) N-[5-(5-Cyclopropyl-[1,3,4]thiadiazol-2-ylsulfamoyl)-indan-2-yl]-2-ethoxy-4-trifluoromethyl-benzamide

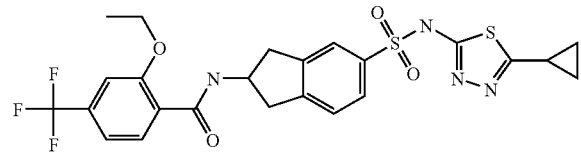

This compound was prepared similarly to the procedure described in example 1 starting from 5-cyclopropyl-[1,3,4]thiadiazol-2-ylamine.
MS (ESI): (M+1)=553

23) 2-Ethoxy-N-[5-(5-phenyl-[1,3,4]thiadiazol-2-ylsulfamoyl)-indan-2-yl]-4-trifluoromethyl-benzamide

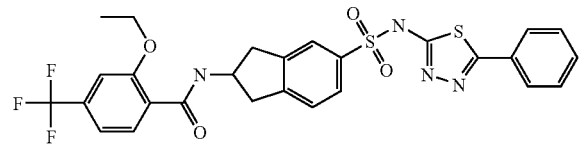

This compound was prepared similarly to the procedure described in example 1 starting from 5-phenyl-[1,3,4]thiadiazol-2-ylamine.
MS (ESI): (M+1)=589

24) 2-Ethoxy-N-[5-(5-cyclohexyl-[1,3,4]thiadiazol-2-ylsulfamoyl)-indan-2-yl]-4-trifluoromethyl-benzamide

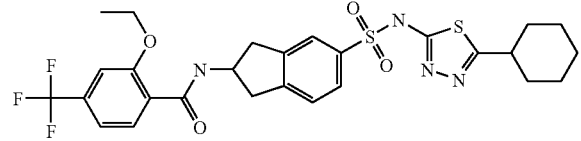

This compound was prepared similarly to the procedure described in example 1 starting from 5-cyclohexyl-[1,3,4]thiadiazol-2-ylamine.
MS (ESI): (M+1)=595

25) 3-Methoxy-pyridine-2-carboxylic acid [5-(5-isopropyl-[1,3,4]thiadiazol-2-ylsulfamoyl)-indan-2-yl]-amide

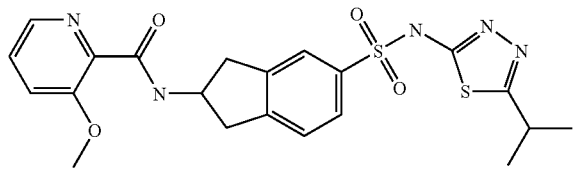

This compound was prepared similarly to the procedure described in example 1 starting from 3-methoxy-pyridine-2-carboxylic acid.
MS (ESI): (M+1)=474

What is claimed is:
1. A compound of formula I:

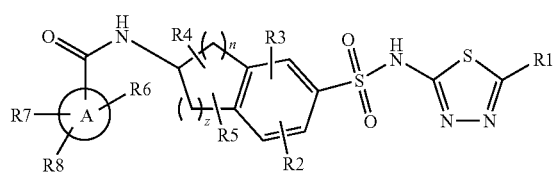

wherein
R1 is selected from the group consisting of (C1-C6)alkyl, (C0-C6)alkylene (C3-C6) cycloalkyl, (C0-C6)alkylene-O—(C1-C6)alkyl, (C0-C6)alkylene-O—(C3-C6) cycloalkyl, (C0-C6)alkylene-(C6-C14)aryl and (C0-C6) alkylene-(C5-C15) heteroaryl, wherein the alkyl, alkylene, aryl, heteroaryl and cycloalkyl can be unsubstituted or mono, di- or trisubstituted by F, Cl, Br, $OCF_3$, CN, CO—(C1-C6) alkyl, COO(C1-C6)alkyl, CON ((C0-C6)alkylene-H)((C0-C6)alkylene-H), or $S(O)_m$ (C1-C6)alkyl;
R2, R3, R4 and R5 are independently selected from the group consisting of H, halogen, (C1-C6)alkyl, (C0-C4) alkylene-O—(C0-C4)alkylene-H, CN, COO(C1-C6) alkyl, CON((C0-C6)alkylene-H)((C0-C6)alkylene-H) and $S(O)_m$(C1-C6)alkyl, wherein the alkyl and alkylene are unsubstituted or mono, di- or trisubstituted by F;
A is (C6-C14)aryl;
n is 1, 2, or 3;
m and z are 0, 1, or 2; and
R6, R7 and R8 are independently selected from the group consisting of H, (C1-C6)alkyl, CN, CO—(C1-C6)alkyl, COO—(C1-C6)alkyl, CON((C0-C6)alkylene-H((C0-C6) alkylene-H), $S(O)_m$(C1-C6)alkyl, N((C0-C6)alkylene-H)((C0-C6)alkylene-H), N((C0-C6)alkylene-H)—CO—(C1-C6)alkyl, N((C0-C6)alkylene-H)—CO—(C1-C6) alkyl, halogen, (C0-C6)alkylene-O—(C0-C6)alkylene-H, (C0-C6)alkylene-O—(C6-C14) aryl, SCF3, S(O)2CF3 and NO2, wherein the alkyl, aryl and alkylene are unsubstituted or mono, di- or trisubstituted by F and the aryl can be unsubstituted or monosubstituted by CF3;
or a stereoisomer, enantiomer, tautomer, or physiologically acceptable salt thereof.
2. The compound according to claim 1, wherein
R1 is selected from the group consisting of (C1-C6)alkyl, (C0-C6)alkylene-(C3-C6) cycloalkyl, (C0-C6)alkylene-O—(C1-C6)alkyl, (C0-C6)alkylene-O—(C3-C6) cycloalkyl and (C0-C6)alkylene-(C6-C14)aryl, wherein the alkyl, alkylene, aryl, and cycloalkyl can be unsubstituted or mono, di- or trisubstituted by F, Cl, or Br;
R2, R3, R4, R5 are independently selected from the group consisting of H, halogen, (C1-C6) alkyl, and (C0-C4) alkylene-O—(C0-C4)alkylene-H, wherein the alkyl and alkylene are unsubstituted or mono, di- or trisubstituted by F;
n is 1, or 2;
z is 1, or 2; and
R6, R7 and R8 are independently selected from the group consisting of H, (C1-C6)alkyl, CN, halogen, (C0-C6) alkylene-O—(C0-C6)alkylene-H, (C0-C6)alkylene-(C6-C14) aryl, (C0-C6)alkylene-O—(C6-C14)aryl, SCF3, and S(O)2CF3, wherein the alkyl, aryl and alkylene are unsubstituted or mono, di- or trisubstituted by F and the aryl can be unsubstituted or monosubstituted by CF3;
or a stereoisomer, enantiomer, tautomer, or physiologically acceptable salt thereof.
3. The compound according to claim 1, wherein
R1 is selected from the group consisting of (C1-C6)alkyl, (C0-C6)alkylene (C3-C6) cycloalkyl and (C0-C6)alkylene-(C6-C14)aryl, wherein the alkyl, alkylene, aryl, and cycloalkyl can be unsubstituted or mono, di- or trisubstituted by F;
R2, R3, R4 and R5 are independently selected from the group consisting of H, halogen, (C1-C6)alkyl and (C0-C4)alkylene-O—(C0-C4)alkylene-H, wherein the alkyl and alkylene are unsubstituted or mono, di- or trisubstituted by F;
A is phenyl;
n is 1;
z is 1;
R6 is F, Cl, Br, or O(C1-C4)-alkyl, and is in the ortho position;
R7 is F, Cl, Br, CH3 or CF3, and is in the para position; and
R8 is H;
or a stereoisomer, enantiomer, tautomer, or physiologically acceptable salt thereof.
4. The compound according to claim 1 wherein
R1 is selected from the group consisting of (C1-C4)alkyl, (C0-C2)alkylene (C3-C6) cycloalkyl and (C0-C2)alkylene-(C6-C10)aryl, wherein the alkyl, aryl, and cycloalkyl can be unsubstituted or mono, di- or trisubstituted by F;
R2 is selected from the group consisting of H, halogen, (C1-C6)alkyl and O—(C0-C4) alkylene-H, wherein the alkyl and alkylene are unsubstituted or mono, di- or trisubstituted by F;
R3 is H;
R4 is H;
R5 is H, or (C1-C4)alkyl;
A is (C6)aryl;
n is 1, or 2;
z is 1;
R6 is selected from the group consisting of (C1-C4)alkyl, halogen, (C0-C2)alkylene-O—(C0-C6)alkylene-H and (C0-C2)alkylene-(C6-C10)aryl, wherein the alkyl, aryl and alkylene are unsubstituted or mono, di- or trisubstituted by F and the aryl can be unsubstituted or monosubstituted by CF3;
R7 is selected from the group consisting of H, (C1-C4) alkyl and halogen, wherein the alkyl is unsubstituted or mono, di- or trisubstituted by F; and
R8 is H or F;
or a stereoisomer, enantiomer, tautomer, or physiologically acceptable salt thereof.
5. The compound according to claim 1, wherein
R1 is selected from the group consisting of (C1-C4)alkyl, (C3-C6)cycloalkyl, and phenyl, wherein the alkyl can be unsubstituted or mono, di- or tri substituted by F;
R2 is selected from the group consisting of H, F, Cl and O—(C1-C4)alkylene-H, wherein the alkylene is unsubstituted or mono, di- or trisubstituted by F;

R3 is H;
R4 is H;
R5 is H or (C1-C4)alkyl;
A is phenyl;
n is 1, or 2;
z is 1;
R6 is selected from the group consisting of (C1-C4)alkyl, F, Cl, O—(C0-C6)alkylene-H, and phenyl, wherein the phenyl can be unsubstituted or monosubstituted by CF3;
R7 is selected from the group consisting of H, (C1-C4) alkyl, and Cl, wherein the alkyl is unsubstituted or mono, di- or trisubstituted by F; and
R8 is H or F;
or a stereoisomer, enantiomer, tautomer, or physiologically acceptable salt thereof.

6. The compound according to claim 1 wherein
R1 is selected from the group consisting of ethyl, isopropyl, tert-butyl, cyclopropyl, cyclohexyl, phenyl and trifluoromethyl;
R2, R3, R4 and R5 are selected from the group consisting of H, F, Cl, CH3 and OCH3;
A is phenyl;
n is 1;
z is 1;
R6 is Cl, Br, or O(C1-C2)-alkyl and is in the ortho position;
R7 is Cl, Br or CF3 and is in the ortho position; and
R8 is H;
or a stereoisomer, enantiomer, tautomer, or physiologically acceptable salt thereof.

7. The compound according to claim 1, wherein
R1 is isopropyl;
R2, R3, R4 and R5 are H;
A is phenyl;
n is 1;
z is 1;
R6 is O(C1-C2)-alkyl, and is in ortho position;
R7 is Cl or CF3 and is in the para position; and
R8 is H;
or a stereoisomer, enantiomer, tautomer, or physiologically acceptable salt thereof.

8. The compound according to claim 1, wherein
R1 is trifluoromethyl;
R2, R3, R4 and R5 are H;
A is phenyl;
n is 1;
z is 1;
R6 is O-ethyl, and is in ortho position;
R7 is Cl or CF3 and is in the para position; and
R8 is H;
or a stereoisomer, enantiomer, tautomer, or physiologically acceptable salt thereof.

9. The compound according to claim 1, wherein
R1 is cyclohexyl;
R2, R3, R4, R5 are H;
A is phenyl;
n is 1;
z is 1;
R6 is O-ethyl and in ortho position;
R7 is Cl or CF3, and is in the para-position; and
R8 is H;
or a stereoisomer, enantiomer, tautomer, or physiologically acceptable salt thereof.

10. The compound according to claim 1, wherein
R1 is phenyl;
R2, R3, R4 and R5 are H;
A is phenyl;
n is 1;
z is 1;
R6 is O-ethyl, and is in ortho position;
R7 is Cl or CF3, and is in para position; and
R8 is H;
or a stereoisomer, enantiomer, tautomer, or physiologically acceptable salt thereof.

11. The compound according to claim 1, wherein
R1 is cyclopropyl;
R2, R3, R4, R5 are H;
A is phenyl;
N is 1;
z is 1;
R6 is O-ethyl and in the ortho-position;
R7 is Cl or CF3 and in the para-position;
R8 is H;
or a stereoisomer, enantiomer, tautomer, or physiologically acceptable salt thereof.

12. A pharmaceutical composition comprising at least one compound according to claim 1, or a stereoisomer, enantiomer, tautomer, or physiologically acceptable salt thereof, in combination with a pharmaceutically acceptable carrier or excipient.

13. The pharmaceutical composition according to claim 12, further comprising at least one additional active pharmaceutical compound, wherein the additional active pharmaceutical compound is effective in the treatment of metabolic disturbance or a physiological disorder associated therewith.

14. The pharmaceutical composition according to claim 13 wherein said additional active pharmaceutical compound is an anti-diabetic compound effective in the treatment of diabetes.

15. The pharmaceutical composition according to claim 13 wherein said additional active pharmaceutical compound is a lipid modulator compound.

16. The pharmaceutical composition according to claim 13 wherein said active pharmaceutical compound is a compound effective in the treatment of metabolic syndrome or a physical manifestation thereof.

17. A process for preparing a pharmaceutical comprising at least one compound according to claim 1, or a stereoisomer, enantiomer, tautomer, or physiologically acceptable salt thereof, in combination with a pharmaceutically acceptable salt thereof, with the pharmaceutically acceptable carrier or excipient, and bringing this mixture into a form suitable for administration.

* * * * *

UNITED STATES PATENT AND TRADEMARK OFFICE
CERTIFICATE OF CORRECTION

PATENT NO.        : 7,612,104 B2
APPLICATION NO.   : 12/062759
DATED             : April 4, 2008
INVENTOR(S)       : Schoenafinger et al.

It is certified that error appears in the above-identified patent and that said Letters Patent is hereby corrected as shown below:

Line 64, column 47 reads

"17. A process for preparing a pharmaceutical comprising at least one compound according to claim 1, or a stereoisomer, enantiomer, tautomer, or physiologically acceptable salt thereof, in combination with a pharmaceutically acceptable salt thereof, with the pharmaceutically acceptable carrier or excipient, and bringing this mixture into a form suitable for administration."

and should read as

--17. A process for preparing a pharmaceutical composition comprising at least one compound according to claim 1, or a stereoisomer, enantiomer, tautomer, or physiologically acceptable salt thereof, in combination with a pharmaceutically acceptable salt thereof, comprising mixing the compound according to claim 1, or the stereoisomer, enantiomer, tautomer, or physiologically acceptable salt thereof, with the pharmaceutically acceptable carrier or excipient, and bringing this mixture into a form suitable for administration.--

Signed and Sealed this

Sixth Day of April, 2010

David J. Kappos
*Director of the United States Patent and Trademark Office*